(12) United States Patent
Penner et al.

(10) Patent No.: US 6,198,965 B1
(45) Date of Patent: Mar. 6, 2001

(54) ACOUSTIC TELEMETRY SYSTEM AND METHOD FOR MONITORING A REJECTION REACTION OF A TRANSPLANTED ORGAN

(75) Inventors: Avi Penner, Tel Aviv; Eyal Doron, Kiryat Yam; Yariv Porat, Haifa, all of (IL)

(73) Assignee: Remon Medical Technologies, Ltd., Caesaria (IL)

(*) Notice: Subject to any disclaimer, the term of this patent is extended or adjusted under 35 U.S.C. 154(b) by 0 days.

(21) Appl. No.: 09/312,760

(22) Filed: May 17, 1999

Related U.S. Application Data

(63) Continuation-in-part of application No. 09/000,553, filed on Dec. 30, 1997, now Pat. No. 6,140,740.

(51) Int. Cl.[7] .................................................. A61B 5/00
(52) U.S. Cl. ............................................................ 600/547
(58) Field of Search ................................... 600/547, 508, 600/510

(56) References Cited

U.S. PATENT DOCUMENTS

| | | | |
|---|---|---|---|
| 3,320,946 | * | 5/1967 | Dethloff et al. ................... 600/547 |
| 4,041,954 | * | 8/1977 | Ohara ................................. 600/510 |
| 5,246,008 | * | 9/1993 | Mueller ............................. 600/508 |

* cited by examiner

Primary Examiner—William E. Kamm

(57) ABSTRACT

A telemetry system for monitoring a rejection reaction of a transplanted organ being transplanted within a patient's body is provided. The telemetry system includes (a) a telemetry control unit located outside the body of the patient; and (b) a telemetry monitoring unit implanted within the body of the patient, the telemetry monitoring unit including: (i) at least one acoustic transducer being for receiving an acoustic signal from the telemetry control unit and converting the acoustic signal into a first electrical signal, the at least one acoustic transducer further being for receiving a second electrical signal and converting the second electrical signal into a transmitted acoustic signal receivable by the telemetry monitoring unit; and (ii) a plurality of electrodes positionable in intimate contact with, or deep within, the transplanted organ and being in communication with the at least one acoustic transducer, the plurality of electrodes being for passing the first electrical signal through the transplanted organ for monitoring the electrical impedance thereof and further being for relaying the second electrical signal corresponding to the electrical impedance to the at least one acoustic transducer so as to enable the monitoring of the presence or absence of the rejection reaction.

21 Claims, 11 Drawing Sheets

ACOUSTIC TELEMETRY SYSTEM AND METHOD FOR MONITORING A REJECTION REACTION OF A TRANSPLANTED ORGAN

This is a continuation-in-part of U.S. patent application Ser. No. 09/000,553, filed Dec. 30, 1997 now U.S. Pat. No. 6,140,740.

FIELD AND BACKGROUND OF THE INVENTION

The present invention relates to a system and method for monitoring a patient for rejection of an implanted organ. More particularly, the system and method of the present invention relate to a telemetry monitoring unit, implanted within the body of a patient which includes an activatable acoustic transducer energizable by an acoustic signal provided from outside the body, such that rejection reactions of an implanted organ such as, for example, an implanted heart, kidney, lung or liver can be monitored and thereby detected as early as possible, while lesser damage has been inflicted upon the transplanted organ, and while immunosuppressive therapy can be most efficiently applied.

Repeated monitoring of physiological parameters associated with certain medical conditions presented by a patient is crucial for effective and timely treatment of such disorders and conditions.

For example, following organ transplantation, rejection of the transplanted organ, especially of a transplanted heart, is a substantial problem often encountered in surgical transplant procedures. As such, it is important to frequently monitor the transplanted organ of the recipient, so as to diagnose a rejection reaction as early as possible in order to be able to institute timely immunosuppressive therapy.

In addition, procedures such as invasive endomyocardial biopsy also neccesitate and employ constant monitoring, often achieved via implantation of hardwire electrodes.

Due to the nature of these medical conditions and further due to limitations inherent to external monitoring devices, implanted monitoring devices are preferably employed in monitoring these conditions. These devices which can be for example, hardwire electrodes, or telemetry devices, relay information pertaining to the condition or disorder to an analysis and recording device positioned outside the body.

Several such telemetry devices which provide information pertaining to physiological parameters associated with medical conditions have been described in the prior art.

For example an implantable telemetry pacemaker, which transmits measured values via an inductive coupling to extracorporeal instruments, see, for example, U.S. Pat. Nos. 4,809,697; 4,585,004; 4,237,900; 4,550,370; and 4,281,664, is used as an implanted monitoring device. These telemetry pacemakers permit repeated monitoring of a patient, by monitoring and measuring electrocardiac rhythms at selected time intervals. In addition, by employing telecommunication systems or by providing a small extracorporeal recording device carried by the patient, monitoring can be effected outside the medical facility.

When using a pacemaker telemeter device as described above, intramyocardial measurements, as effected for example, on a transplanted heart, are oftentimes unreliable since measured results are often influenced by for example, variations of daily electrocardiac rhythm, the exertion state of the patient and the medication ingested by the patient. Thus a drop of the measured cardiac voltage signals is not necessarily due to, and indicative of, an incipient rejection reaction.

An example of a more accurate system for monitoring a transplanted organ is disclosed in U.S. Pat No. 5,246,008 which describes a battery powered measuring system implanted on the monitored organ for providing data, as electromagnetic radiation, relating to the electrophysiological condition of the organ. The disclosed system is based on the knowledge that functional changes of organs and especially functional changes of the heart are associated with changes of the electrophysiological properties of the tissue, which changes can be detected by a change of the electrical impedance of the tissue (see, for example, B. C. Penney et al., Medical & Biological Engineering & Computing, 1985, 23, p. 1–7; Pfitzmann R, Muller J, Grauhan O. Cohnert T, Hetzer R, Z Kardiol, 1998, Measuring bioelectric myocardial impedance as a non invasive method for diagnosis of graft rejection after heart transplantation, 87(4):258–266; Hetzer R. et al., 1998, Daily non-invasive rejection monitoring improves long-term survival in pediatric heart transplantation, Ann. Thorac. Surg. (66):1343–1349; Pirolo J S, Shuman T S, Brunt E M, Liptay M J, Cox J L, Ferguson T B Jr., J Thorac Cardiovasc Surg, 1992, Non invasive detection of cardiac allograft rejection by prospective telemetric monitoring, 103(5):969–79; Bonnefoy E, Ninet J, Robin J, Leroux F, Boissonat P, Brule P, Champsaur G., 1994, Bipolar intramyocardial electrogram from an implanted telemetric pacemaker for the diagnosis of cardiac allograft rejection, Pacing Clin Electrophysiol, 17(11 Pt 2):2052–6; Gerhausser A, Reichel T, Neukomm P A, Bolz A, Hugel J, Schaldach M, 1997, Diagnosis of rejection after kidney transplantation by impedance spectroscopy with an implantable measuring system, Biomed Tech (Berl), 42 Suppl. 160-1, which are incorporated herein by reference).

The electrical impedance is a complex variable having both amplitude and phase. For a given alternating voltage, V, of the form:

$$V = A \cdot e^{i\omega}$$

the resulting current, I, is:

$$I = B \cdot e^{i(\omega t - \phi)}$$

where A and B are the voltage and current amplitude, respectively, ω is the frequency, i is the square root of −1, t is time and φ is the relative phase between the voltage and the current.

The electrical impedance, Z, is defined as:

$$Z = V/I$$

or more specifically as:

$$Z = |Z| \cdot e^{i\phi}$$

where |Z|≡A/B is the absolute value of the electrical impedance.

It is believed that the changes in electrical impedance are due to interstitial edemas, infiltration in the interstitial tissues and electrophysiological changes of the cell membranes and of their resistive and capacitive properties.

Although measuring tissue impedance is considered a more accurate method to predict heart tissue rejection, accurate and efficient monitoring using the above described system is impeded by several limitations due to the utilization thereby of electromagnetic radiation to establish telemetry between the implanted monitor and an extracorporeal controlling and recording device.

Since the electromagnetic radiation transmitted into the body by an extracorporeal unit of this system does not supply sufficient power to energize the implanted monitor, a battery is included within the implanted monitor.

In addition, since electromagnetic radiation does not penetrate body tissues well, this system necessitates additional electrical leads which are wire connected to the monitoring device and implanted close to the body surface for receiving the electromagnetic radiation and relaying it to the implanted monitor. This power manifestation drastically decreases the time period for which the device can be employed within the body since batteries are exhaustible. In addition since this system necessitates implantation of two interwired components in different locations of the body, the implantation procedure is rendered complicated and the chances of infection are increased.

Moreover, since the prior art devices require electrical wires for energy supply and communication, it is not practical to implant such devices deep within an organ. Since some physiological changes are initiated deep within the organ, remote from its surface, it is advantageous to measure the impedance deep within in the transplanted organ.

There is thus a widely recognized need for, and it would be highly advantageous to have, a system and method for monitoring a patient for rejection reactions of an implanted organ devoid of the above limitations, which system is implanted power source free and has further advantages as further detailed hereinunder.

SUMMARY OF THE INVENTION

According to one aspect of the present invention there is provided a telemetry system for monitoring a rejection reaction of a transplanted organ being transplanted within a patient's body, the telemetry system comprising (a) a telemetry control unit located outside the body of the patient; and (b) a telemetry monitoring unit implanted within the body of the patient, the telemetry monitoring unit including: (i) at least one acoustic transducer being for receiving an acoustic signal from the telemetry control unit and converting the acoustic signal into a first electrical signal, the at least one acoustic transducer further being for receiving a second electrical signal and converting the second electrical signal into a transmitted acoustic signal receivable by the telemetry monitoring unit; and (ii) a plurality of electrodes positionable in intimate contact with, or deep within, the transplanted organ and being in communication with the at least one acoustic transducer, the plurality of electrodes being for passing the first electrical signal through the transplanted organ for monitoring the electrical impedance thereof and further being for relaying the second electrical signal corresponding to the electrical impedance to the at least one acoustic transducer so as to enable the monitoring of the presence or absence of the rejection reaction.

According to another aspect of the present invention there is provided a method of monitoring a rejection reaction of a transplanted organ being transplanted within a patient's body, the method comprising the steps of (a) implanting a telemetry monitoring unit including a plurality of electrodes and at least one acoustic transducer communicating therewith within a patient's body, the plurality of electrodes being in intimate contact with, or deep within, the transplanted organ; (b) locating a telemetry control unit located outside, and in intimate contact with, the body of the patient; (c) generating an acoustic signal via the telemetry control unit, the acoustic signal impinging on the transducer of the telemetry monitoring unit, being transduced into a first electrical signal, being relayed to the plurality of electrodes and being passed through the transplanted organ to thereby provide information pertaining to an impedance of the transplanted organ in a form of a second electrical signal being relayed from the plurality of electrodes to the transducer; and (d) receiving via the telemetry control unit a second acoustic signal being transmitted thereto by the transducer, the second acoustic signal corresponding to the second electrical signal.

According to further features in preferred embodiments of the invention described below the transplanted organ is an internal organ.

According to still further features in the described preferred embodiments the internal organ is selected from the group consisting of a heart, a kidney, a liver and a lung.

According to still further features in the described preferred embodiments the at least one acoustic transducer includes (i) a cell member having a cavity; (ii) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (iii) a first electrode attached to the external surface and a second electrode attached to the internal surface.

According to still further features in the described preferred embodiments the first electrical signal is passed by a first pair of the plurality of electrodes and further wherein the second electrical signal is relayed by a second pair of the plurality of electrodes.

According to still further features in the described preferred embodiments the electrical impedance is measured using two epicardial leads (such as Medtronic CapSure EPI 4965-35) positioned at the right and left ventricles.

According to still further features in the described preferred embodiments the first pair of the plurality of electrodes and the second pair of the plurality of electrodes are a single pair of electrodes.

According to still further features in the described preferred embodiments the first electrical signal is supplied as an alternating electrical current, such that a phase shift of the voltage relative to the current phase indicative of the impedance is relayed by the second electrical signal.

According to still further features in the described preferred embodiments the first electrical signal is a substantially square wave pulse electrical current, such that a change in the pulse's amplitude and or phase shift of the complex impedance value indicative of the impedance is relayed by the second electrical signal.

According to still further features in the described preferred embodiments the height and the steepness of the leading edges of the square wave pulse are relayed by the second electrical signal and monitored.

According to still further features in the described preferred embodiments the plurality of electrodes are arranged in a grid form.

The present invention successfully addresses the shortcomings of the presently known configurations by providing a telemetry monitoring system and method for acoustically monitoring a rejection reaction of a transplanted organ, transplanted in the body of a patient, rendering the telemetry system implanted power source free.

BRIEF DESCRIPTION OF THE DRAWINGS

The invention herein described, by way of example only, with reference to the accompanying drawings, wherein:

FIG. 2a is a cross section of a transducer element according to the present invention taken along line C—C in FIG. 1a;

FIG. 2b is a cross section of a transducer element according to the present invention taken along line D—D in FIG. 1a;

FIG. 2c is a cross section of a transducer element according to the present invention taken along line E—E in FIG. 1a;

FIG. 2d is a cross section of a transducer element according to the present invention taken along line F—F in FIG. 1a;

FIG. 2e is a cross section of a transducer element according to the present invention taken along line G—G in FIG. 1a;

FIG. 13b is a side cutaway view of the telemetry monitoring unit of FIG. 13a.

DESCRIPTION OF THE PREFERRED EMBODIMENTS

Figure 1A:
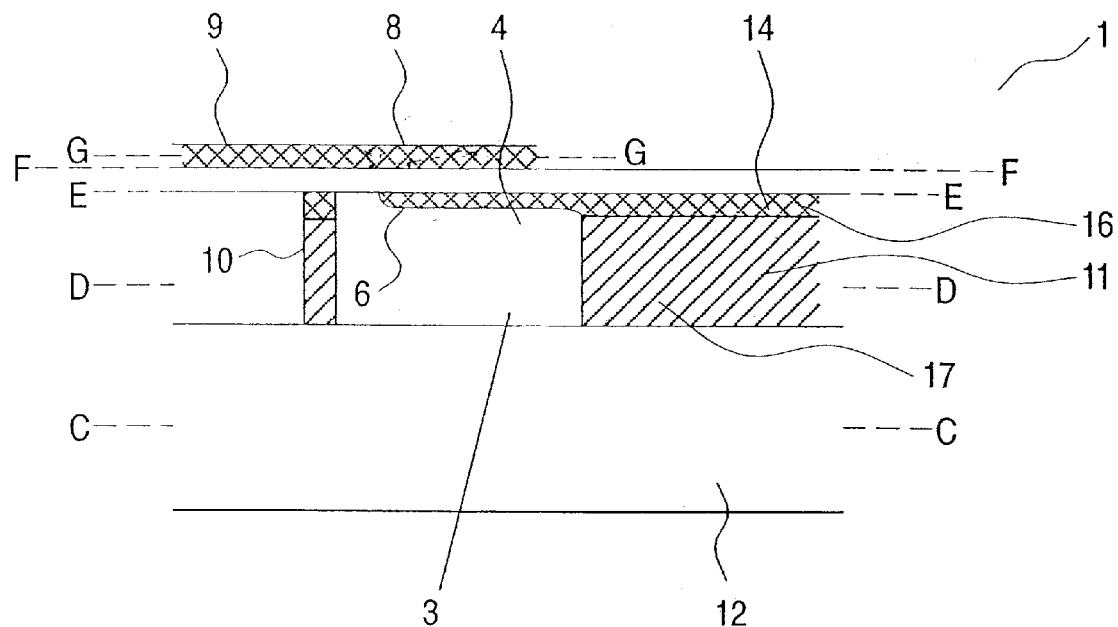
FIG. 1a is a longitudinal section of a transducer element according to the present invention taken along lines A—A in FIGS. 2a–2e.

The present invention is of a system and method which can be used for telemetrically monitoring a patient for a rejection reaction of a transplanted organ. Specifically, the present invention can be used to monitor the rejection reaction of a transplanted organ, such as, for example, a heart, by transmitting data pertaining to the electrical conductance of the transplanted organ via an acoustic telemetry monitoring unit implanted in the body.

The principles and operation of a system and method for telemetrically monitoring a patient for a rejection reaction of a transplanted organ according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For purposes of better understanding the system and method according to the present invention, as illustrated in FIGS. 10–13b of the drawings, reference is first made to the construction and operation of a transducer as described in U.S. patent application Ser. No. 09/000,553.

Referring now to the drawings, FIGS. 1a, 1b and 2a–2e illustrate a preferred embodiment of a transducer element according to the present invention which is referred to herein as transducer element 1. Transducer element 1 serves for converting received acoustic signals into electrical power and for converting electrical power to transmitted acoustic signals. As shown in the figures, the transducer element 1 includes at least one cell member 3 including a cavity 4 etched into a substrate and covered by a substantially flexible piezoelectric layer 2. Attached to piezoelectric layer 2 are an upper electrode 8 and a lower electrode 6, the electrodes for connection to an electronic circuit.

The substrate is preferably made of an electrical conducting layer 11 disposed on an electrically insulating layer 12, such that cavity 4 is etched substantially through the thickness of electrically conducting layer 11.

Electrically conducting layer 11 is preferably made of copper or gold and insulating layer 12 is preferably made of a polymer such as polyimide or PVDF. Conventional copper-plated polymer laminate such as KAPTON™ sheets may be used for the production of transducer element 1. Commercially available laminates such as NOVACLAD™ may be used. Alternatively, the substrate may include a silicon layer, or any other suitable material. Alternatively, layer 11 is made of a non-conductive material such as PYRALIN™.

Preferably, cavity 4 is etched into the substrate by using conventional printed-circuit photolithography methods. Alternatively, cavity 4 may be etched into the substrate by using VLSI/micro-machining technology or any other suitable technology.

Piezoelectric layer 2 may be made of PVDF or a copolymer thereof. Alternatively, piezoelectric layer 2 is made of a substantially flexible piezoceramic. Preferably, piezoelectric layer 2 is a poled PVDF sheet having a thickness of about 9–28 μm. Preferably, the thickness and radius of flexible layer 2, as well as the pressure within cavity 4, are specifically selected so as to provide a predetermined resonant frequency. When using the embodiment of FIGS. 1a and 1b, the radius of layer 2 is defined by the radius of cavity 4.

By using a substantially flexible piezoelectric layer 2, the invention described in U.S. patent application Ser. No. 09/000,553 allows to provide a miniature transducer element whose resonant frequency is such that the acoustic wavelength is much larger than the extent of the transducer. This enables the transducer to be omnidirectional even at resonance, and further allows the use of relatively low frequency acoustic signals which do not suffer from significant attenuation in the surrounding medium.

Prior art designs of miniature transducers, however, rely on rigid piezoceramic usually operating in thickness mode. In such cases the resonant frequency relates to the size of the element and speed of sound in the piezoceramic, and is higher by several orders of magnitude.

The invention described in U.S. patent application Ser. No. 09/000,553 provides a transducer which is omnidirectional, i.e., insensitive to the direction of the impinging acoustic rays, thereby substantially simplifying the transducer's operation relative to other resonant devices. Such a transducer element is thus suitable for application in confined or hidden locations, where the orientation of the transducer element cannot be ascertained in advance.

According to a specific embodiment, cavity 4 features a circular or hexagonal shape with radius of about 200 $\mu$m. Electrically conducting layer 11 preferably has a thickness of about 15 $\mu$m. Cell member 3 is preferably etched completely through the thickness of electrically conducting layer 11. Electrically insulating layer 12 preferably features a thickness of about 50 $\mu$m. The precise dimensions of the various elements of a transducer element according to the invention described in U.S. patent application Ser. No. 09/000,553 may be specifically tailored according to the requirements of the specific application.

Cavity 4 preferably includes a gas such as air. The pressure of gas within cavity 4 may be specifically selected so as to predetermine the sensitivity and ruggedness of the transducer as well as the resonant frequency of layer 2.

Figure 2A:
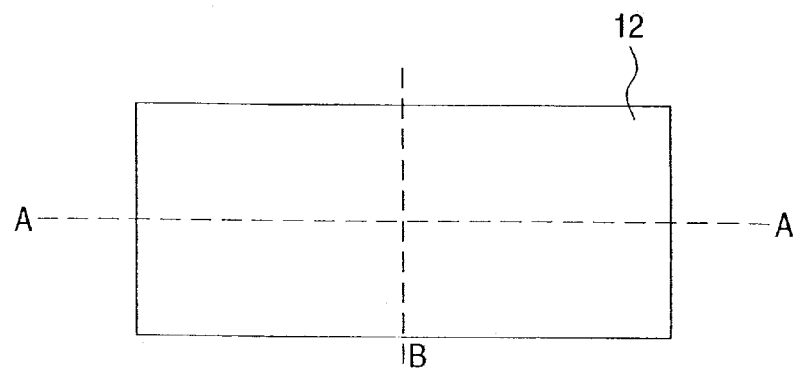
Figure 2B:
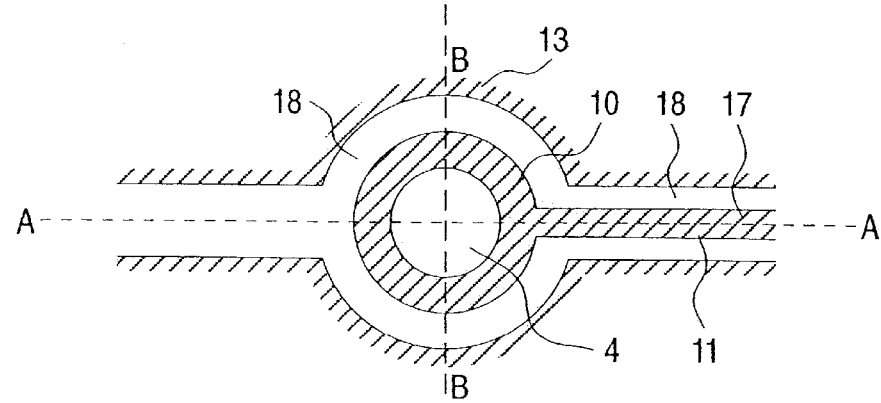

As shown in FIG. 2b, an insulating chamber 18 is etched into the substrate, preferably through the thickness of conducting layer 11, so as to insulate the transducer element from other portions of the substrate which may include other electrical components such as other transducer elements etched into the substrate. According to a specific embodiment, the width of insulating chamber 18 is about 100 $\mu$m. As shown, insulating chamber 18 is etched into the substrate so as to form a wall 10 of a predetermined thickness enclosing cavity 4, and a conducting line 17 integrally made with wall 10 for connecting the transducer element to another electronic component preferably etched into the same substrate, or to an external electronic circuit.

Figure 1B:
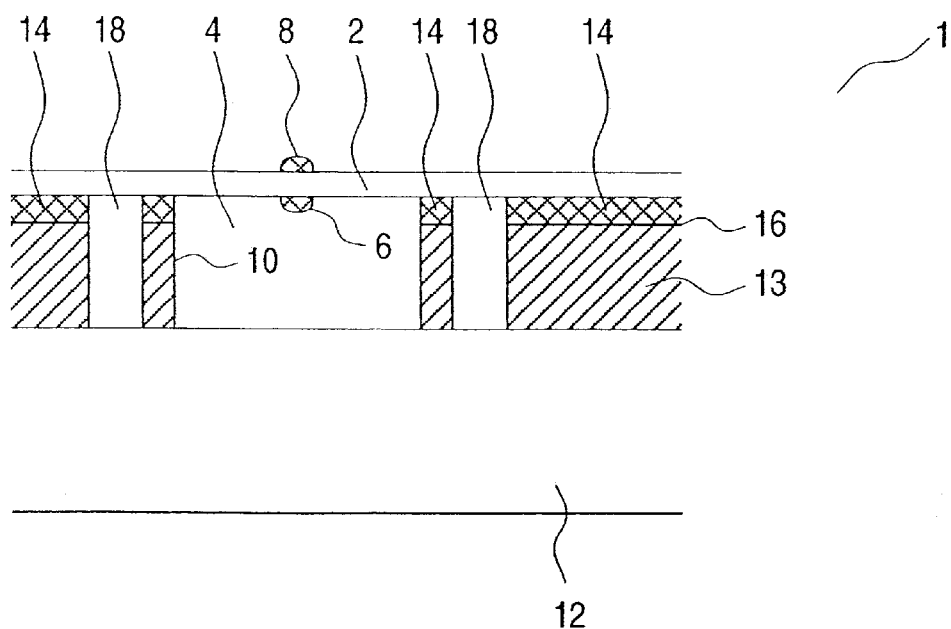
FIG. 1b is a longitudinal section of a transducer element according to the present invention taken along lines B—B in FIGS. 2a–2e.
Figure 2C:
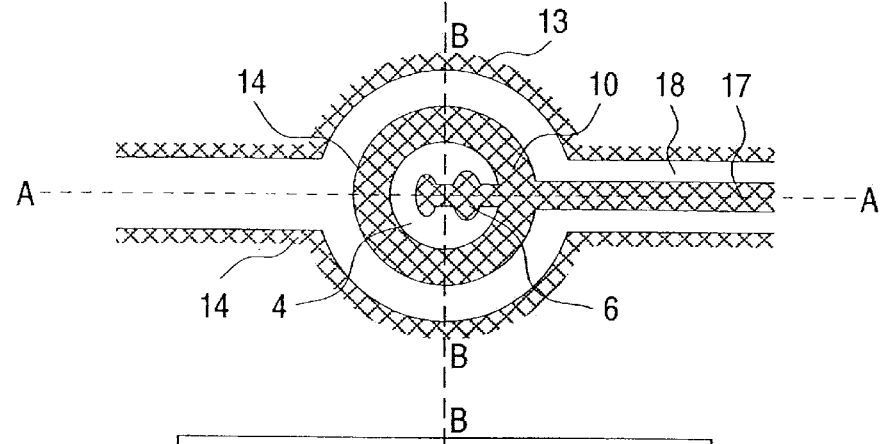
Figure 2D:
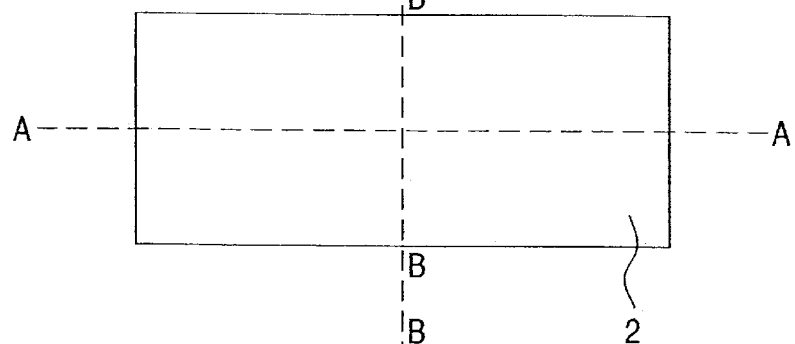
Figure 2E:
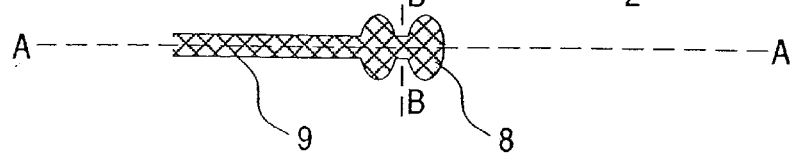

As shown in FIGS. 1a and 1b, attached to piezoelectric layer 2 are upper electrode 8 and lower electrode 6. As shown in FIGS. 2c and 2e, upper electrode 8 and lower electrode 6 are preferably precisely shaped, so as to cover a predetermined area of piezoelectric layer 2. Electrodes 6 and 8 may be deposited on the upper and lower surfaces of piezoelectric membrane 2, respectively, by using various methods such as vacuum deposition, mask etching, painting, and the like.

As shown in FIG. 1a, lower electrode 6 is preferably made as an integral part of a substantially thin electrically conducting layer 14 disposed on electrically conducting layer 11. Preferably, electrically conducting layer 14 is made of a NickeLCopper alloy and is attached to electrically conducting layer 11 by mechanism of a sealing connection 16. Sealing connection 16 may be made of indium. According to a preferred configuration, sealing connection 16 may feature a thickness of about 10 $\mu$m, such that the overall height of wall 10 of cavity 4 is about 20–25 $\mu$m.

As shown in FIG. 2c, electrically conducting layer 14 covers the various portions of conducting layer 11, including wall 10 and conducting line 17. The portion of conducting layer 14 covering conducting line 17 is for connection to an electronic component, as further detailed hereinunder.

According to a preferred embodiment, electrodes 6 and 8 are specifically shaped to include the most energy-productive region of piezoelectric layer 2, so as to provide maximal response of the transducer while optimizing the electrode area, and therefore the cell capacitance, thereby maximizing a selected parameter such as voltage sensitivity, current sensitivity, or power sensitivity of the transducer element.

The vertical displacement of piezoelectric layer 2, $\Psi$, resulting from a monochromatic excitation at angular frequency $\omega$ is modeled using the standard equation for thin plates:

$$(\nabla^2 - \gamma^2)(\nabla^2 + \gamma^2)\Psi - \frac{3(1-\nu^2)}{2Qh^2}P + \frac{3iZ\omega(1-\nu^2)}{2Qh^3}\overline{\Psi} = 0$$

wherein Q is the Young's modulus representing the elasticity of layer 2; h the half-thickness of layer 2; $\nu$ is the Poisson ratio for layer 2; $\gamma$ is the effective wavenumber in the layer given by: $\gamma^4 = 3\rho(1-\nu^2)\omega^2/Qh^2$, wherein $\rho$ is the density of layer 2 and $\omega$ is the angular frequency of the applied pressure (wherein the applied pressure may include the acoustic pressure, the static pressure differential across layer 2 and any other pressure the transducer comes across); Z is the mechanical impedance resulting from the coupling of layer 2 to both external and internal media of cavity 4, wherein the internal medium is preferably air and the external medium is preferably fluid; P is the acoustic pressure applied to layer 2, and $\overline{\Psi}$ represents the average vertical displacement of layer 2.

When chamber 4 is circular, the solution (given for a single frequency component $\omega$) representing the dynamic displacement of a circular layer 2 having a predetermined radius a, expressed in polar coordinates, is:

$$\Psi(r, \varphi) = \frac{I_1(\gamma a)[J_0(\gamma r) - J_0(\gamma a)] + J_1(\gamma a)[I_0(\gamma r) - I_0(\gamma a)]}{2h\rho\omega^2 L_0(\gamma a) + i\omega Z L_2(\gamma a)} P$$

$$L_0(z) = I_0(z)J_1(z) + J_0(z)I_1(z), \; L_2(z) = J_2(z)I_1(z) - I_2(z)J_1(z)$$

$$Z = \frac{P_A}{i\omega H_A} + i\left[\frac{4}{3\pi} + \frac{1}{6}\right]\omega\rho_W a$$

wherein $\Psi(r,\phi)$ is time-dependent and represents the displacement of a elected point located on circular layer 2, the specific location of which is given by radius r and angle $\phi$; J and I are the normal and modified Bessel functions of the first kind, respectively; $P_A$, $H_A$ are the air pressure within cavity 4 and the height of chamber 4, respectively; and $\rho_W$ is the density of the fluid external to cavity 4.

The first term of the impedance Z relates to the stiffness resulting from compression of air within cavity 4, and the second term of Z relates to the mass added by the fluid boundary layer. An additional term of the impedance Z relating to the radiated acoustic energy is substantially negligible in this example.

The charge collected between electrodes 6 and 8 per unit area is obtained by evaluating the strains in layer 2 resulting from the displacements, and multiplying by the pertinent off-diagonal elements of the piezoelectric strain coefficient tensor, $e_{31}$, $e_{32}$, as follows:

$$Q(r, \varphi, t) = e_{31}\left(\frac{\partial \Psi}{\partial x}\right)^2 + e_{32}\left(\frac{\partial \Psi}{\partial y}\right)^2$$

wherein $Q(r,\phi,t)$ represents the charge density at a selected point located on circular layer 2, the specific location of which is given by radius r and angle $\phi$; x is the stretch direction of piezoelectric layer 2; y is the transverse direction (the direction perpendicular to the stretch direction) of layer 2; $e_{31}$, $e_{32}$ are off-diagonal elements of the piezoelectric strain coefficient tensor representing the charge accumulated at a selected point on layer 2 due to a given strain along the x and y directions, respectively, which coefficients being substantially dissimilar when using a PVDF layer. $\Psi$ is the displacement of layer 2, taken as the sum of the displacement for a given acoustic pressure P at frequency f, and the static displacement resulting from the pressure differential between the interior and exterior of cavity 4, which displacements being extractable from the equations given above.

The total charge accumulated between electrodes 6 and 8 is obtained by integrating $Q(r,\phi,t)$ over the entire area S of the electrode:

$$Q = \int_S Q(r,\phi,t) d\vec{x}$$

The capacitance C of piezoelectric layer 2 is given by:

$$C = \frac{\varepsilon}{2h} \int_S d\vec{x},$$

wherein $\varepsilon$ is the dielectric constant of piezoelectric layer 2; and 2h is the thickness of piezoelectric layer 2.

Accordingly, the voltage, current and power responses of piezoelectric layer 2 are evaluated as follows:

$$V = \frac{2h \int_S S(r, \varphi, t) d\vec{x}}{\varepsilon \int_S d\vec{x}}, \quad I = 2i\omega \int_S Q(r, \varphi, t) d\vec{x},$$

$$W = \frac{4ih\left[\int_S Q(r, \varphi, t) d\vec{x}\right]^2}{\varepsilon \int_S d\vec{x}}$$

The DC components of Q are usually removed prior to the evaluation, since the DC currents are usually filtered out. The values of Q given above represent peak values of the AC components of Q, and should be modified accordingly, so as to obtain other required values such as RMS values.

According to the above, the electrical output of the transducer expressed in terms of voltage, current and power responses depend on the AC components of Q, and on the shape S of the electrodes. Further, as can be seen from the above equations, the voltage response of the transducer may be substantially maximized by minimizing the area of the electrode. The current response, however, may be substantially maximized by maximizing the area of the electrode.

Figure 3:
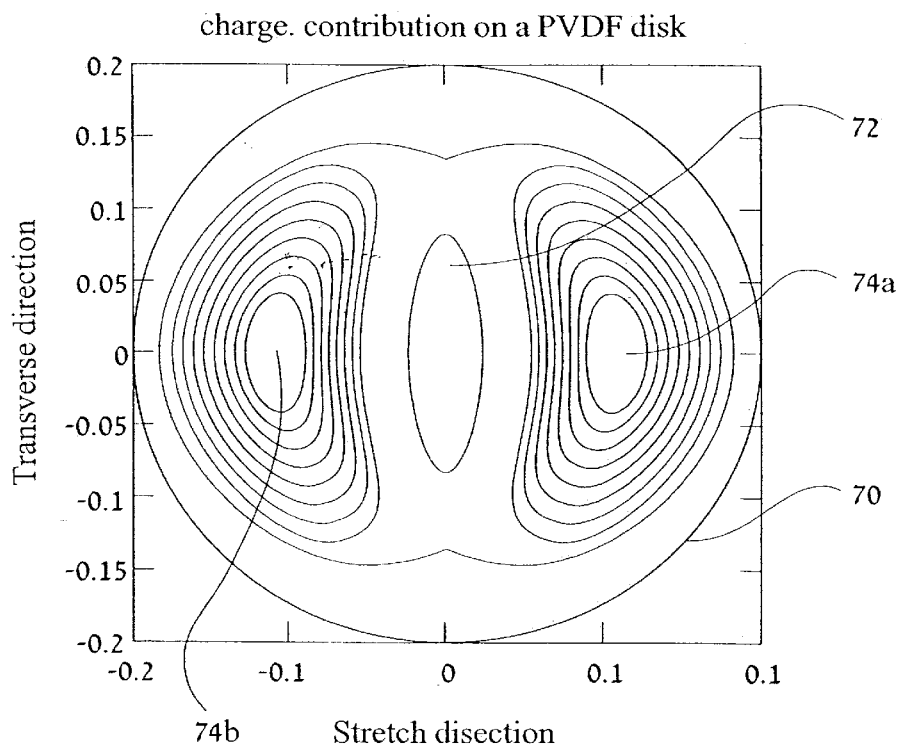
FIG. 3 shows the distribution of charge density across a piezoelectric layer of a transducer element resulting from the application of a constant pressure over the entire surface of the layer.

FIG. 3 shows the distribution of charge density on a circular piezoelectric layer 2 obtained as a result of pressure (acoustic and hydrostatic) applied uniformly over the entire area of layer 2, wherein specific locations on layer 2 are herein defined by using Cartesian coordinates including the stretch direction (x direction) and the transverse direction (y direction) of layer 2. It can be seen that distinct locations on layer 2 contribute differently to the charge density. The charge density vanishes at the external periphery 70 and at the center 72 of layer 2 due to minimal deformation of these portions. The charge density is maximal at two cores 74a and 74b located symmetrically on each side of center 72 due to maximal strains (in the stretch direction) of these portions.

A preferred strategy for optimizing the electrical responses of the transducer is to shape the electrode by selecting the areas contributing at least a selected threshold percentage of the maximal charge density, wherein the threshold value is the parameter to be optimized. A threshold value of 0% relates to an electrode covering the entire area of layer 2.

Figure 4:
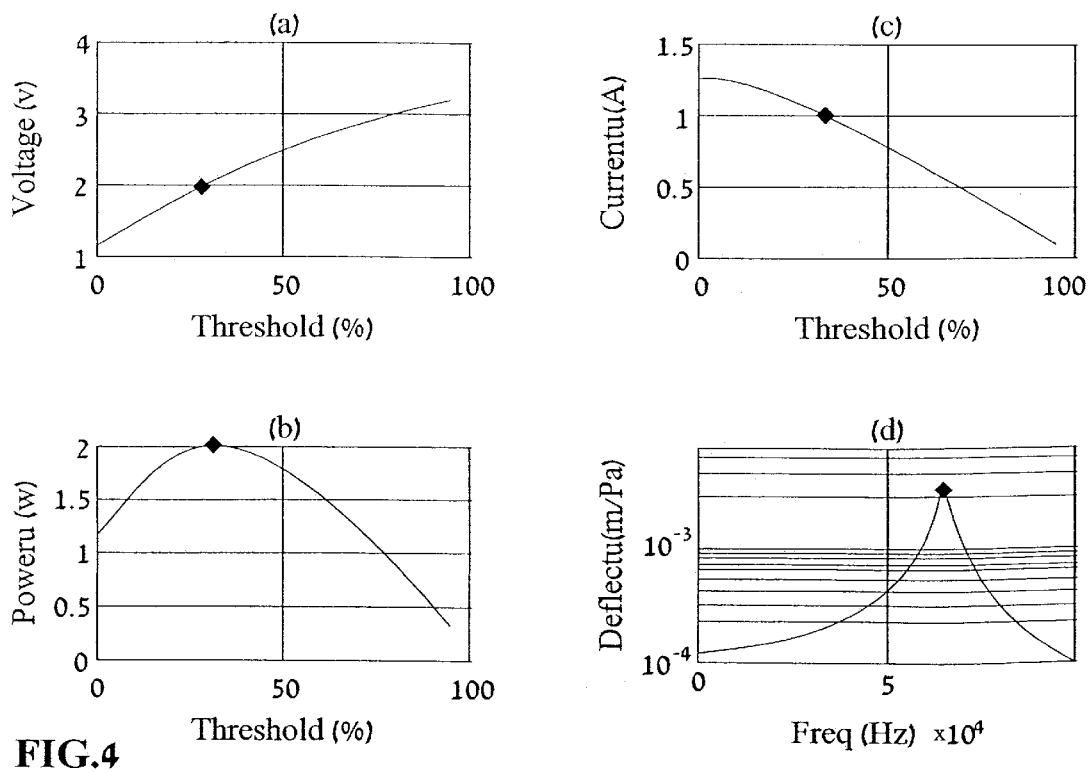
FIG. 4 shows the results of optimization performed for the power response of a transducer according to the present invention.

FIG. 4 shows the results of an optimization performed for the power response of a transducer having a layer 2 of a predetermined area. As shown in the Figure, the threshold value which provides an optimal power response is about 30% (graph b). Accordingly, an electrode which covers only the portions of layer 2 contributing at least 30% of the maximal charge density yields a maximal power response. The pertinent voltage response obtained by such an electrode is higher by a factor of 2 relative to an electrode completely covering layer 2 (graph a). The current response obtained by such electrode is slightly lower relative to an electrode completely covering layer 2 (graph c). Further as shown in the Figure, the deflection of layer 2 is maximal when applying an acoustic signal at the resonant frequency of layer 2 (graph d).

Figure 5:
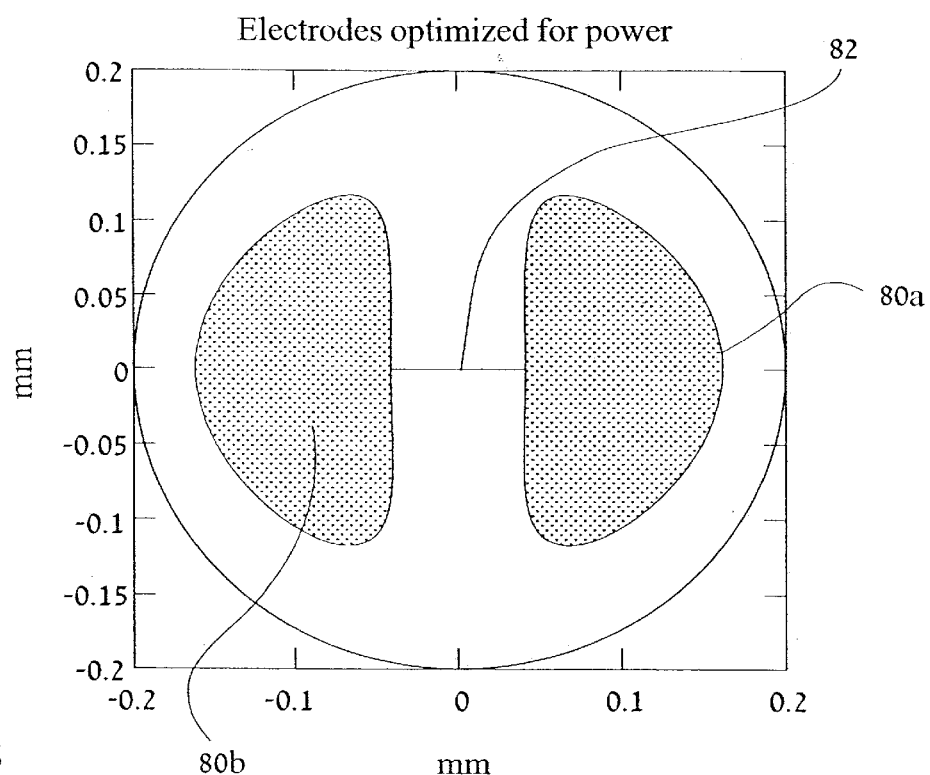
FIG. 5 shows a preferred electrode shape for maximizing the power response of a transducer according to the present invention.

A preferred electrode shape for maximizing the power response of the transducer is shown in FIG. 5, wherein the electrode includes two electrode portions 80a and 80b substantially covering the maximal charge density portions of layer 2, the electrode portions being interconnected by mechanism of a connecting member 82 having a minimal area. Preferably, portions 80a and 80b cover the portions of layer 2 which yield at least a selected threshold (e.g. 30%) of the maximal charge density.

According to the present invention any other parameter may be optimized so as to determine the shape of electrodes 6 and 8. According to further features of the invention described in U.S. patent application Ser. No. 09/000,553, only one electrode (upper electrode 8 or lower electrode 6) may be shaped so as to provide maximal electrical response of the transducer, with the other electrode covering the entire area of layer 2. Since the charge is collected only at the portions of layer 2 received between upper electrode 8 and lower electrode 6, such configuration is operatively equivalent to a configuration including two shaped electrodes having identical shapes.

Figure 6:
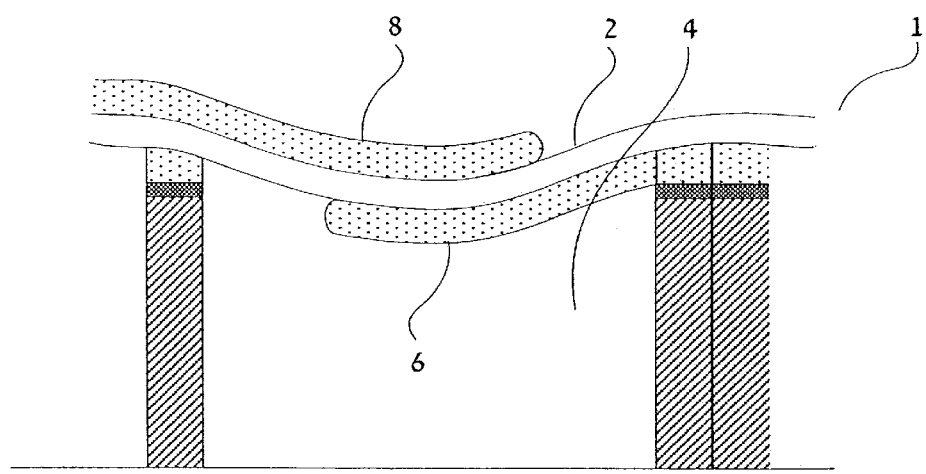
FIG. 6 is a longitudinal section of another embodiment of a transducer element according to the present invention capable of functioning as a transmitter.

Referring now to FIG. 6, according to another embodiment chamber 4 of transducer element 1 may contain gas of substantially low pressure, thereby conferring a substantially concave shape to piezoelectric membrane 2 at equilibrium. Such configuration enables to further increase the electrical response of the transducer by increasing the total charge obtained for a given displacement of layer 2. The total displacement in such an embodiment is given by: $\Psi = P_0 \Psi_{DC} + P\Psi_{AC} \cos \omega t$, wherein $P_0$ is the static pressure differential between the exterior and the interior of cavity 4; $\Psi_{DC}$ is the displacement resulting from $P_0$; P is the amplitude of the acoustic pressure; and $\Psi_{AC}$ is the displacement resulting from P.

Accordingly, the strain along the x direction includes three terms as follows:

$$S_{xx} = \left(\frac{\partial \Psi}{\partial x}\right)^2$$

$$= P_0^2 \left(\frac{\partial \Psi_{DC}}{\partial x}\right)^2 + P^2 \left(\frac{\partial \Psi_{AC}}{\partial x}\right)^2 \cos^2 \omega t +$$

$$2 P_0 P \frac{\partial \Psi_{DC}}{\partial x} \frac{\partial \Psi_{AC}}{\partial x} \cos \omega t$$

wherein the DC component is usually filtered out.

Thus, by decreasing the pressure of the medium (preferably air) within cavity 4 relative to the pressure of the external medium (preferably fluid), the value of $P_0$ is increased, thereby increasing the value of the third term of the above equation.

Such embodiment makes it possible to increase the charge output of layer 2 for a given displacement, thereby increasing the voltage, current and power responses of the transducer without having to increase the acoustic pressure P. Furthermore, such embodiment enables to further miniaturize the transducer since the same electrical response may be obtained for smaller acoustic deflections. Such embodiment is substantially more robust mechanically and therefore more durable than the embodiment shown in FIGS. 1*a* and 1*b*. Such further miniaturization of the transducer enables to use higher resonance frequencies relative to the embodiment shown in FIGS. 1*a* and 1*b*.

Preferably, a transducer element 1 according to the invention described in U.S. patent application Ser. No. 09/000,553 is fabricated by using technologies which are in wide use in the microelectronics industry, so as to allow integration thereof with other conventional electronic components as further detailed hereinunder. When the transducer element includes a substrate such as Copper-polymer laminate or silicon, a variety of conventional electronic components may be fabricated onto the same substrate.

According to a preferred embodiment, a plurality of cavities 4 may be etched into a single substrate 12 and covered by a single piezoelectric layer 2, so as to provide a transducer element including a matrix of transducing cell members 3, thereby providing a larger energy collecting area of predetermined dimensions, while still retaining the advantage of miniature individual transducing cell members 3. When using such configuration, the transducing cell members 3 may be electrically interconnected in parallel or serial connections, or combinations thereof, so as to tailor the voltage and current response of the transducer. Parallel connections are preferably used so as to increase the current output while serial connections are preferably used so as to increase the voltage output of the transducer.

Furthermore, piezoelectric layer 2 may be completely depolarized and then repolarized at specific regions thereof, so as to provide a predetermined polarity to each of the transducing cell members 3. Such configuration enables to reduce the complexity of interconnections between cell members 3.

A transducer element according to the invention described in U.S. patent application Ser. No. 09/000,553 may be further used as a transmitter for transmitting information to a remote receiver by modulating the reflection of an external impinging acoustic wave arrived from a remote transmitter.

Referring to FIG. 6, the transducer element shown may function as a transmitter element due to the asymmetric fluctuations of piezoelectric layer 2 with respect to positive and negative transient acoustic pressures obtained as a result of the pressure differential between the interior and exterior of cavity 4.

A transmitter element according to the present invention preferably modulates the reflection of an external impinging acoustic wave by mechanism of a switching element connected thereto. The switching element encodes the information that is to be transmitted, such as the output of a sensor, thereby frequency modulating a reflected acoustic wave.

Such configuration requires very little expenditure of energy from the transmitting module itself, since the acoustic wave that is received is externally generated, such that the only energy required for transmission is the energy of modulation.

Specifically, the reflected acoustic signal is modulated by switching the switching element according to the frequency of a message electric signal arriving from another electronic component such as a sensor, so as to controllably change the mechanical impedance of layer 2 according to the frequency of the message signal.

Preferably, a specific array of electrodes connected to a single cell member or alternatively to a plurality of cell members are used, so as to control the mechanical impedance of layer 2.

Figure 7A:
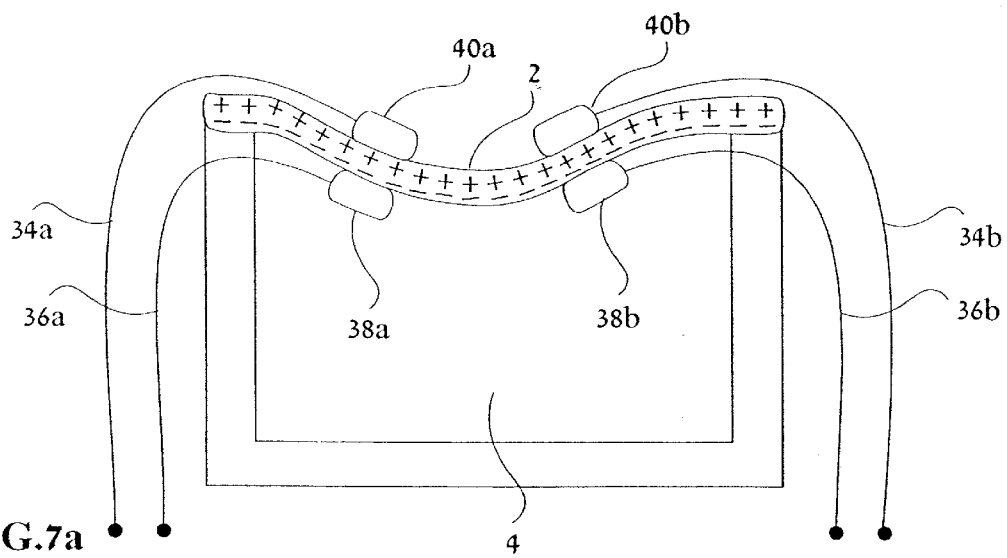
FIGS. 7a–7f are schematic views of possible configurations of transmitters according to the present invention including parallel and anti-parallel electrical connections for controllably changing the mechanical impedance of the piezoelectric layer.

FIGS. 7*a*–7*g* illustrate possible configurations for controllably change the impedance of layer 2 of a transmitter element. Referring to FIG. 7*a*, a transmitter element according to the invention described in U.S. patent application Ser. No. 09/000,553 may include a first and second pairs of electrodes, the first pair including an upper electrode 40*a* and a lower electrode 38*a*, and the second pair including an upper electrode 40*b* and a lower electrode 38*b*. Electrodes 38*a*, 38*b*, 40*a* and 40*b* are electrically connected to an electrical circuit by mechanism of conducting lines 36*a*, 36*b*, 34*a* and 34*b*, respectively, the electrical circuit including a switching element (not shown), so as to alternately change the electrical connections of conducting lines 36*a*, 36*b*, 34*a* and 34*b*.

Preferably, the switching element switches between a parallel connection and an anti-parallel connection of the electrodes. A parallel connection decreases the mechanical impedance of layer 2, wherein an anti-parallel connection increases the mechanical impedance of layer 2. An anti-parallel connection may be obtained by interconnecting line 34*a* to 36*b* and line 34*b* to 36*a*. A parallel connection may be obtained by connecting line 34*a* to 34*b* and line 36*a* to 36*b*. Preferably, the switching frequency equals the frequency of a message signal arriving from an electrical component such as a sensor as further detailed hereinunder.

Figure 7B:
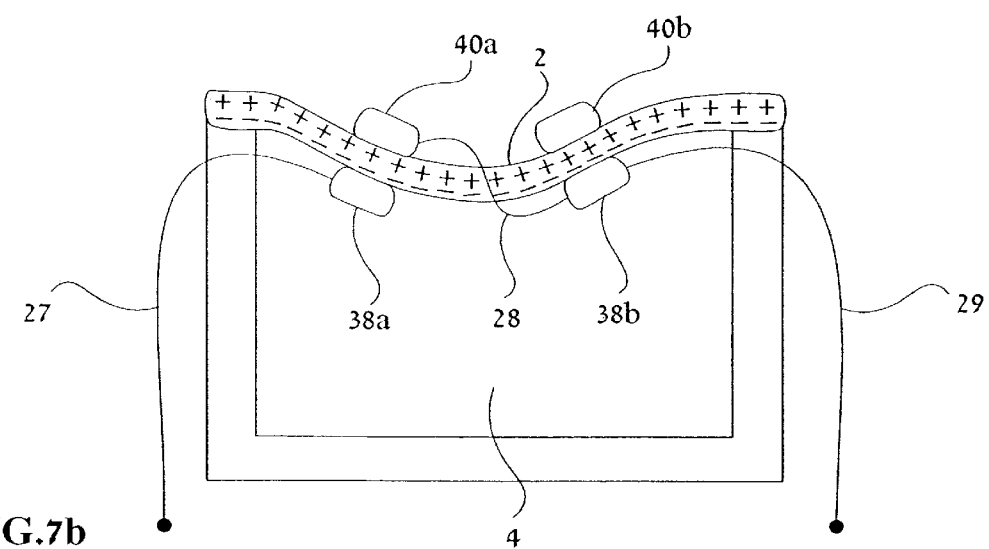

According to another embodiment shown in FIG. 7*b*, upper electrode 40*a* is connected to lower electrode 38*b* by mechanism of a conducting line 28, and electrodes 38*a* and 40*b* are connected to an electrical circuit by mechanism of conducting lines 27 and 29, respectively, wherein the electrical circuit further includes a switching element. Such configuration provides an anti-parallel connection of the electrodes, wherein the switching element functions as an on/off switch, thereby alternately increasing the mechanical impedance of layer 2.

Figure 7C:
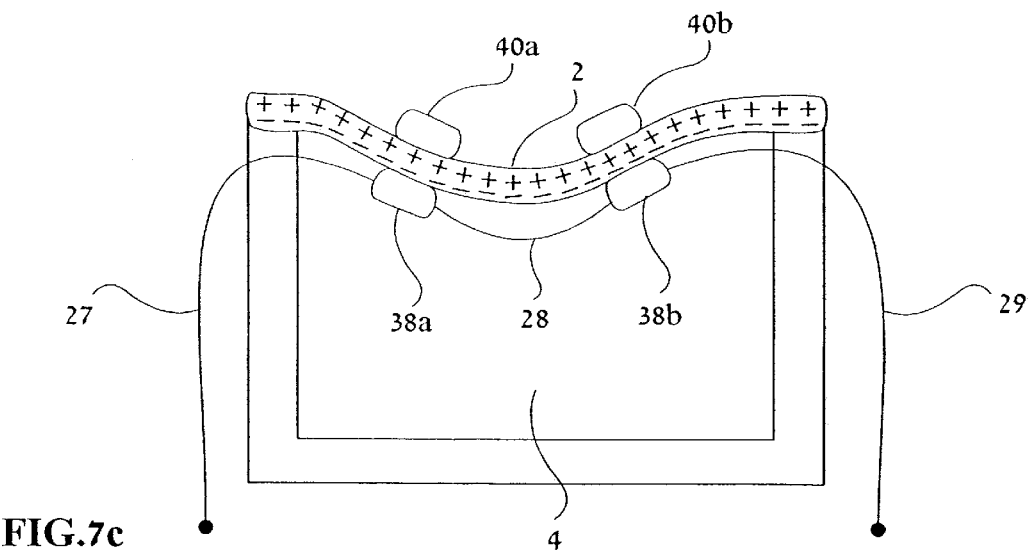

In order to reduce the complexity of the electrical connections, layer 2 may be depolarized and then repolarized at specific regions thereof. As shown in FIG. 7*c*, the polarity of the portion of layer 2 received between electrodes 40*a* and 38*a* is opposite to the polarity of the portion of layer 2 received between electrodes 40*b* and 38*b*. An anti-parallel connection is thus achieved by interconnecting electrodes 38*a* and 38*b* by mechanism of a conducting line 28, and providing conducting lines 27 and 29 connected to electrodes 40*a* and 40*b*, respectively, the conducting lines for connection to an electrical circuit including a switching element.

According to another embodiment, the transmitting element includes a plurality of transducing cell members, such that the mechanical impedance of layer 2 controllably changed by appropriately interconnecting the cell members.

Figure 7D:
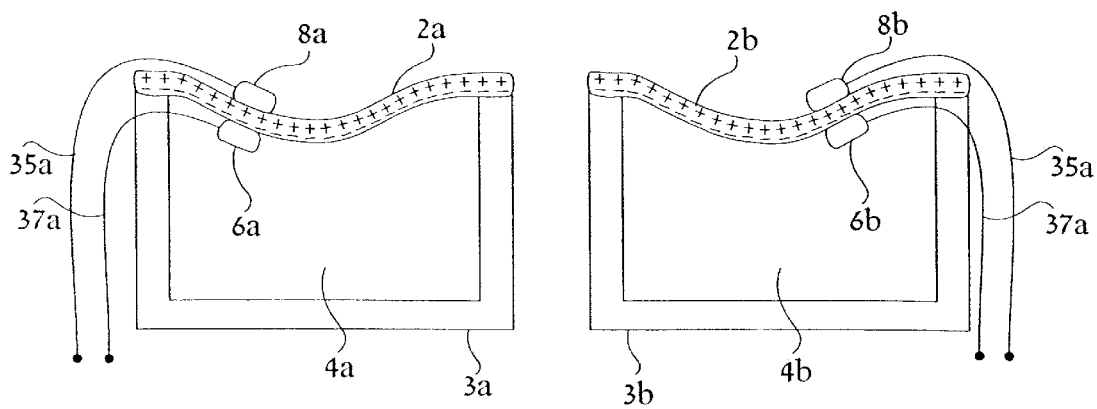

As shown in FIG. 7d, a first transducing cell member 3a including a layer 2a and a cavity 4a, and a second transducing cell member 3b including a layer 2b and a cavity 4b are preferably contained within the same substrate; and layers 2a and 2b are preferably integrally made. A first pair of electrodes including electrodes 6a and 8a is attached to layer 2, and a second pair of electrode including electrodes 6b and 8b is attached to layer 2b. Electrodes 6a, 8a, 6b and 8b are electrically connected to an electrical circuit by mechanism of conducting lines 37a, 35a, 37b and 35b, respectively, the electrical circuit including a switching element, so as to alternately switch the electrical connections of conducting lines 37a, 35a, 37b and 35b, so as to alternately provide parallel and anti-parallel connections, substantially as described for FIG. 7a, thereby alternately decreasing and increasing the mechanical impedance of layers 2a and 2b.

Figure 7E:
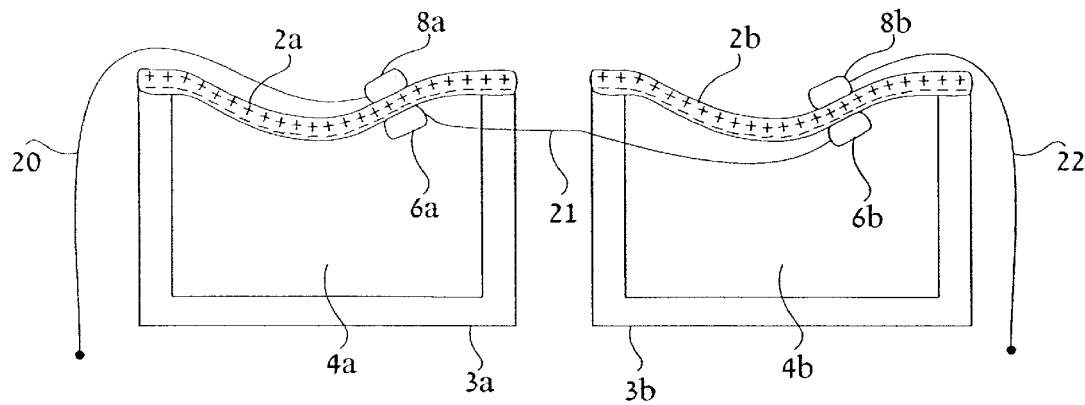

FIG. 7e illustrates another embodiment, wherein the first and second transducing cell members are interconnected by mechanism of an anti-parallel connection. As shown in the Figure, the polarity of layer 2a is opposite to the polarity of layer 2b, so as to reduce the complexity of the electrical connections between cell members 3a and 3b. Thus, electrode 6a is connected to electrode 6b by mechanism of a conducting line 21, and electrodes 8a and 8b are provided with conducting lines 20 and 22, respectively, for connection to an electrical circuit which includes a switching element, wherein the switching element preferably functions as an on/off switch, so as to alternately increase the mechanical impedance of layers 2a and 2b.

Figure 7F:
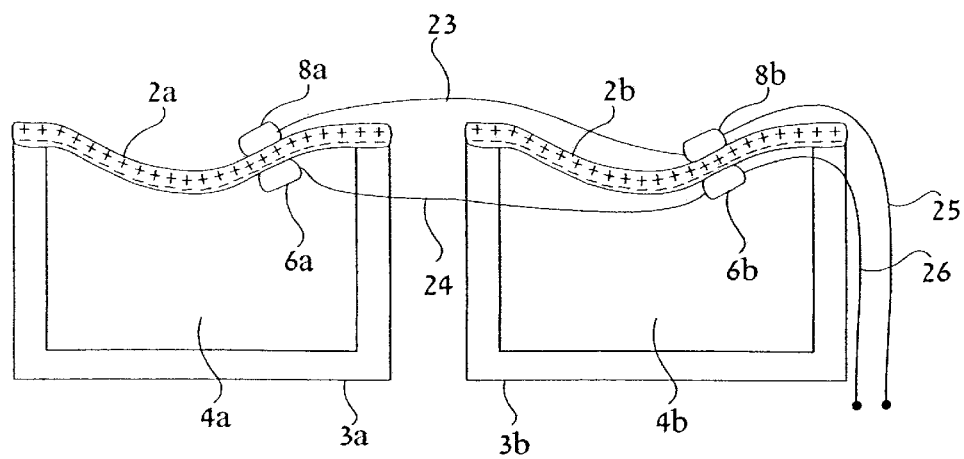

FIG. 7f shows another embodiment, wherein the first and second transducing cell members are interconnected by mechanism of a parallel connection As shown, electrodes 6a and 6b are interconnected by mechanism of conducting line 24, electrodes 8a and 8b are interconnected by mechanism of conducting line 23, and electrodes 6b and 8b are provided with conducting lines 26 and 25, respectively, the conducting lines for connection to an electrical circuit including a switching element. The switching element preferably functions as an on/off switch for alternately decreasing and increasing the mechanical impedance of layers 2a and 2b.

Figure 8:
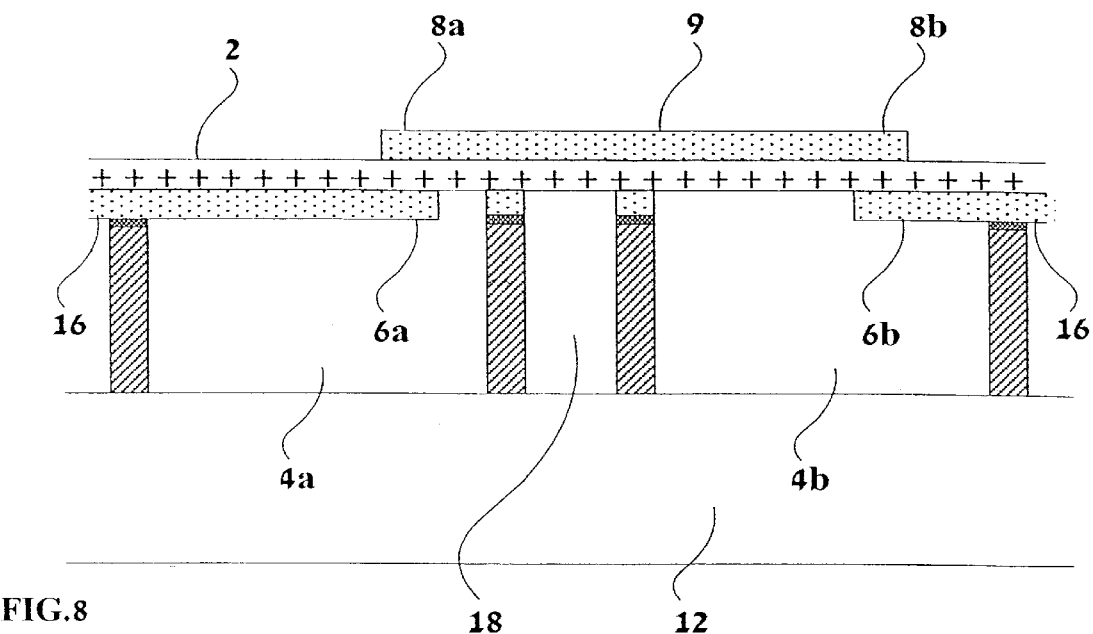
FIG. 8 is a longitudinal section of a transmitter element according to the present invention including an anti-parallel electrical connection.

FIG. 8 shows a possible configuration of two transducing cell members etched onto the same substrate and interconnected by mechanism of an anti-parallel connection. As shown in the Figure, the transducing cell members are covered by a common piezoelectric layer 2, wherein the polarity of the portion of layer 2 received between electrodes 6a and 8a is opposite to the polarity of the portion of layer 2 received between electrodes 6b and 8b. Electrodes 8a and 8b are bonded by mechanism of a conducting line 9, and electrodes 6a and 6b are provided with conducting lines 16 for connection to an electrical circuit.

Figure 9:
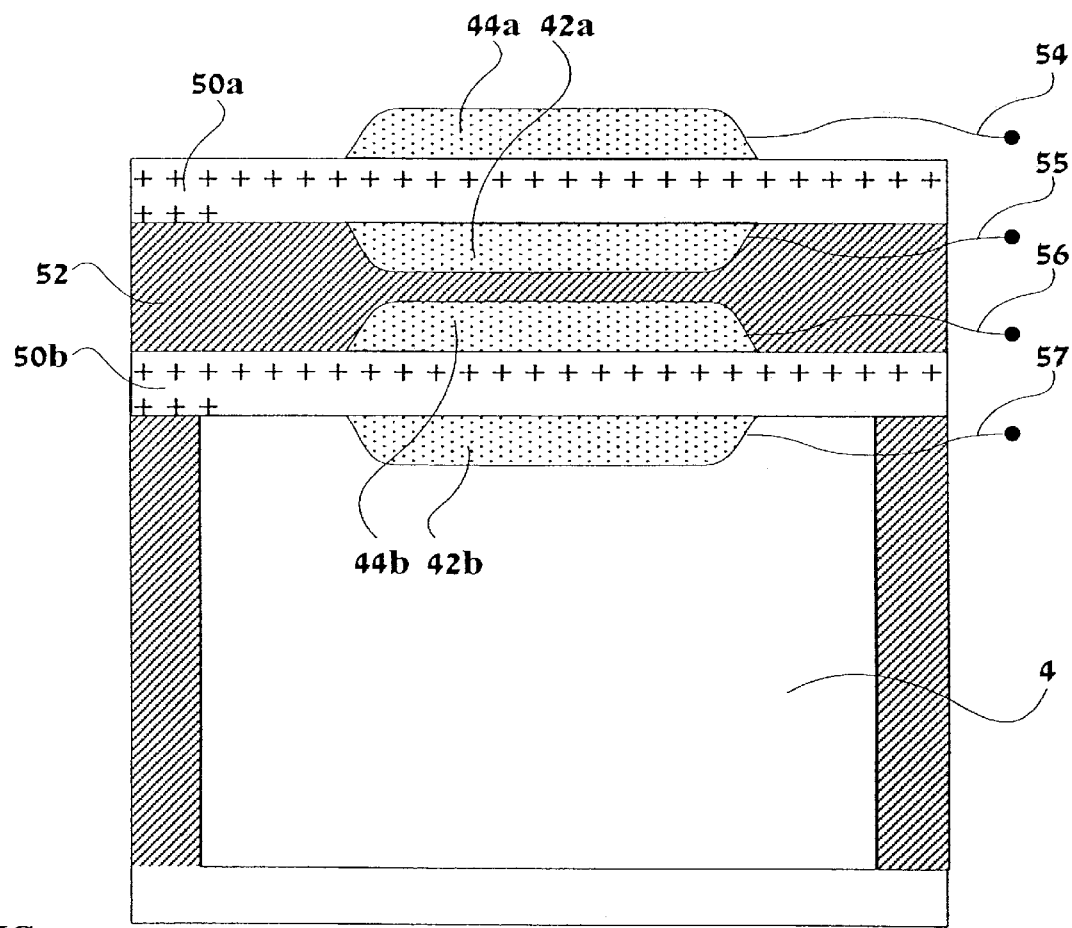
FIG. 9 is a longitudinal section of another embodiment of a transmitter element according to the present invention.

Another embodiment of a transmitter element according to the present invention is shown in FIG. 9. The transmitter element includes a transducing cell member having a cavity 4 covered by a first and second piezoelectric layers, 50a and 50b, preferably having opposite polarities. Preferably, layers 50a and 50b are interconnected by mechanism of an insulating layer 52. Attached to layer 50a are upper and lower electrodes 44a and 42a, and attached to layer 50b are upper and lower electrodes 44b and 42b. Electrodes 44a, 42a, 44b and 42b are provided with conducting lines 54, 55, 56 and 57, respectively, for connection to an electrical circuit.

It will be appreciated that the above descriptions are intended only to serve as examples, and that many other embodiments are possible within the spirit and the scope of invention described in U.S. patent application Ser. No. 09/000,553.

As is detailed hereinunder, in preferred embodiments, the present invention exploits the advantages of the acoustic transducer described hereinabove and in U.S. patent application Ser. No. 09/000,553.

According to one aspect of the present invention there is provided a telemetry system for monitoring a rejection reaction of an organ transplanted within a patient's body which is referred to hereinunder as system 100.

Referring again to the drawings, FIGS. 10–13b illustrate some of the components included in system 100 according to the present invention.

Figure 10:
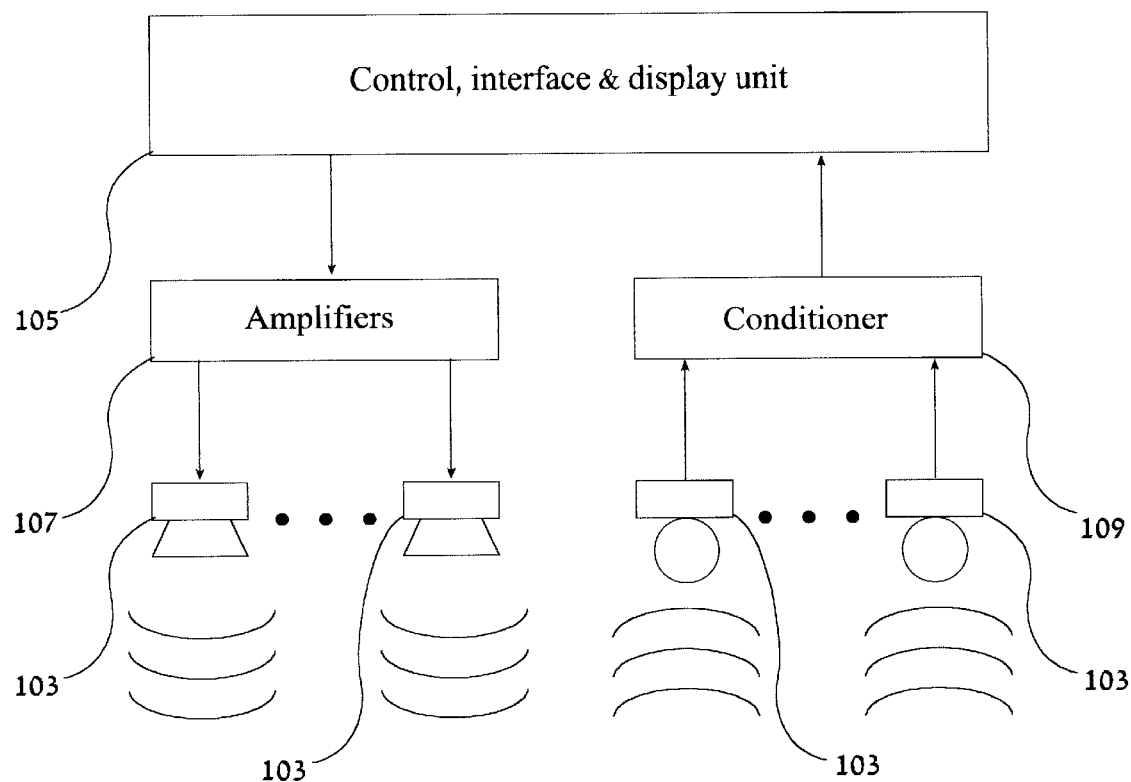
FIG. 10 is a block diagram depicting the components of the extracorporeal telemetry control unit of the present invention.

As shown in FIG. 10, system 100 includes a telemetry control unit 102 located outside the body of the patient. Telemetry control unit 102 serves for generating and transmitting a transmitted acoustic signal and for receiving, analyzing and displaying information from received acoustic signals. To this end, telemetry control unit includes at least one extracorporeal transducer 103 (four are shown) which serves both to receive and to transmit an acoustic signal. Telemetry control unit 102 further includes amplifiers 107, conditioners 109 and a control, interface and display unit 105. In order for unit 102 to transmit an acoustic signal a command is given by unit 105 and an electrical signal is generated thereby. This signal is amplified via amplifiers 107 and finally it is converted into an acoustic signal by transducer 103. It will be appreciated that concomitantly with this conversion, the acoustic signal generated is transmitted from transducer 103. In addition, when an acoustic signal impinges on transducer 103, it is converted via transducer 103 to an electrical signal which is conditioned via conditioner 109 to increase the signal-to-noise ratio and is thereafter relayed to unit 105 for analysis and display. It will be appreciated that each of transducers 103 can serve according to different embodiments of the present invention as a receiver, a transmitter or a transceiver. In the latter case, amplifiers 107 and conditioners 109 can be integrated into a single unit operatively communicating with a transducer 103 which functions both as a receiver and as a transmitter (i.e., transceiver).

As further shown in FIGS. 11–13b monitoring system 100 further includes a telemetry monitoring unit 104 which is, when in use, implanted in intimate contact with, or deep within, a transplanted organ of the patient, which transplanted organ can be, for example, of a human donor or a xenograft transplant.

According to a preferred embodiment of the present invention telemetry monitoring unit 104 includes within a housing 110 thereof an acoustic intrabody transducers 106 and 106', which serve as a receiver and a transmitter, respectively. It will, however, be appreciated that a single transducer which serves both as a receiver and as a transmitter (i.e., as a transceiver) of acoustic signals can be used to replace transducers 106 and 106'.

Unit 104 further includes a pair of transmitting electrodes 108 and relaying electrodes 112 positioned within housing 110. Electrodes 108 serve for passing a first electric signal though the transplanted organ. Electrodes 112 serve for relaying information relating to the impedance of the transplanted organ, as a second electric signal. To this end, and as specifically shown in FIG. 12, when unit 104 is implanted in a patient's body, measures are undertaken to ensure that electrodes 108 and 112 of unit 104 are placed in intimate contact with, or deep within, the transplanted organ being monitored.

Electrodes 108 and 112 are electrically coupled to transducers 106 and 106' preferably via an interface 111 which can include electrical wiring or other electrical coupling devices well known in the art of electronics. Optionally and according to another preferred embodiment of the present invention the function of pairs of electrodes 108 and 112 are assumed by a single pair of electrodes which serves the function of both electrodes 108 and 112. Other electrode configurations can also be used in combination with the telemetry monitoring system such as, for example, those described in U.S. Pat. No. 5,246,008 which is incorporated herein by reference.

It is known that organ rejection is characterized by local changes in cell physiology which occur in small millimetric portions of the organ. Although these physiological changes originate from small millimetric portions of the organ, the resultant physiological change influences larger portions of the organ, and as a result, the generated impedance can be masked by effects associated with such changes. However, since the statistical variance of the measured impedance in a rejected organ is substantially larger than the statistical variance of impedance observed in normal healthy tissue, measuring the tissue impedance at several points and calculating the tissue average impedance provides means for measuring the impedance variance. Such measurements can be effected, for example, using electrodes located in a grid form as further detailed hereinunder with respect to FIG. 14.

In order to effect monitoring of a rejection reaction of a transplanted organ in accordance with the teachings of the present invention, telemetry control unit 102 (FIG. 10) is placed in intimate contact with, or deep within, the body of the patient and an acoustic signal is transmitted therefrom by extracorporeal transducer 103. This signal, when impinging on transducer 106, is received thereby and is concomitantly converted into an electrical power signal for powering monitoring unit 104 and for relaying an electrical current through the tissue of the transplanted organ. This signal can also include a unique device activation code provided as digitized information in cases where multiple telemetry monitoring systems of a single or different types are used.

According to a preferred embodiment, the converted electric power signal is relayed as an alternating electric current to electrodes 108. Electrodes 108 pass the electrical current through the tissue of the transplanted organ. Substantially at the same time, electrodes 112 measure the impedance absolute value and phase of the tissue through which the current is flowing.

As used herein in the specification and in the claims section that follows, the term, "impedance" refers to the total opposition to alternating current by an electric circuit, resulted by ohmic resistance, capacitance and induction of the circuit.

Preferably electrodes 108 and 112 are made of a metal having good electrical conductivity and which is medically accepted for transplantations, such as, for example, gold, silver, platinum, iridium or alloys thereof.

To provide accurate measurements electrodes 108 and 112 are preferably constructed in close proximity thereamongst, and extruding from housing 110 such that the same region of tissue in which the current is flowing is also measured for impedance. Preferably, housing 110 is made of an electrically insulating material, that is tolerated by the body, such as, for example, silicon rubber, polyurethane, PVDF and the like.

As mentioned above, electrodes 108 preferably pass the first electric signal as an alternating current through the tissue of the transplanted organ such that information pertaining to the impedance absolute value and phase characterizing the transplanted organ to the electrical signal is relayed to transducer 106' via a second electrical signal collected from the tissue by electrodes 112.

It will be appreciated by one ordinarily skilled in the art that the impedance substantially depends on the ohmic resistance and the capacitance of the tissue. The ohmic resistance itself depends substantially on the electrical properties of the extracellular space present between cells composing the tissue, whereas the capacitance depends substantially on the electrical properties of the cell membrane. During a rejection reaction, and as a result of ischemia of the tissue being rejected, an intracellular edema with simultaneous shrinkage of the extracellular space occurs. As a result, both the ohmic resistance and the capacitance of the tissue are changed resulting in a monitorable change of the tissue impedance.

Preferably, a square-wave voltage pulse is used to generate the alternating current. An alteration in the pulse form following its passage through the transplanted organ, and the phase shift between the current and the voltage, can, for example, serve according to preferred embodiments of the invention for monitoring the impedance of the transplanted tissue. As further detailed hereinbelow these data correspond to information relayable by electrodes 112 to transducer 106 as a second electrical signal.

Transducer 106' receives the second electrical signal from electrodes 112 and converts this electrical signal into a transmitted acoustic signal which is receivable by transducer 103 of telemetry control unit 102. The function of telemetry unit 102 is further detailed hereinabove with respect to FIG. 10.

To enable the conversion of an electrical signal into an acoustic signal and vice versa, intrabody transducers 106 and 106' and extracorporeal transducer(s) 103 are assembled in a fashion as described hereinabove with respect to transducer element 1, the construction of which is further detailed with regard to FIGS. 1a, 1b and 2a–2e. Alternatively, a plurality of transducer elements 1 can also be utilized in various configurations (as shown in, and described in respect to, for example, FIGS. 7b–f, 8 and 9 hereinabove) in transducers 106 and 106' of telemetry monitoring unit 104 and/or in transducers 103 or telemetry control unit 102 of the present invention.

As mentioned above, telemetry monitoring unit 104 serves for relaying information pertaining to a rejection reaction of a transplanted organ to telemetry control unit 102 which is positioned outside the body.

As further detailed above, to effect this function, telemetry monitoring unit 104 includes electrodes 108 and 112 and transducers 106 and 106'.

Figure 11:
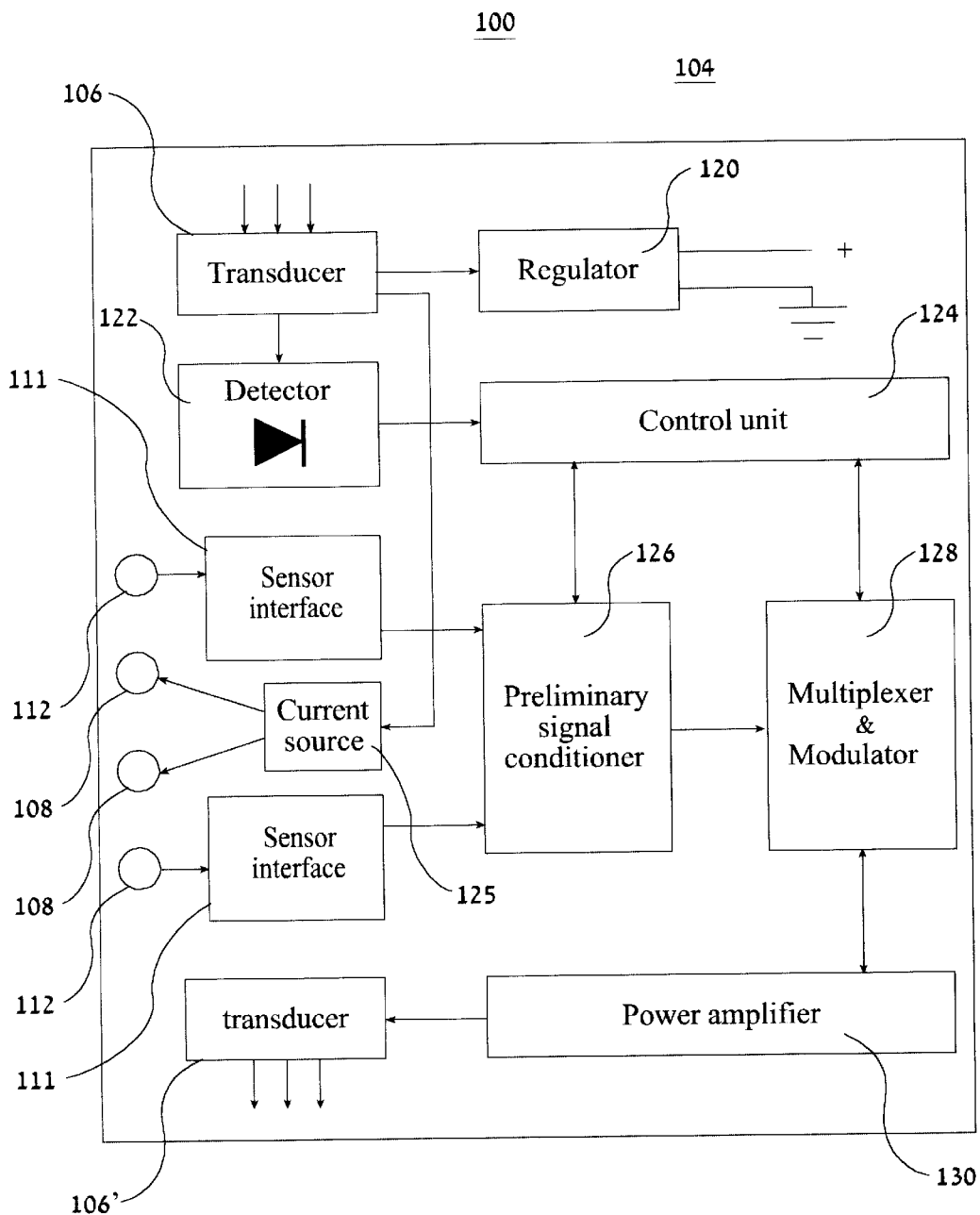
FIG. 11 is a block diagram depicting the components of the intrabody telemetry monitoring unit of the present invention.
Figure 12:
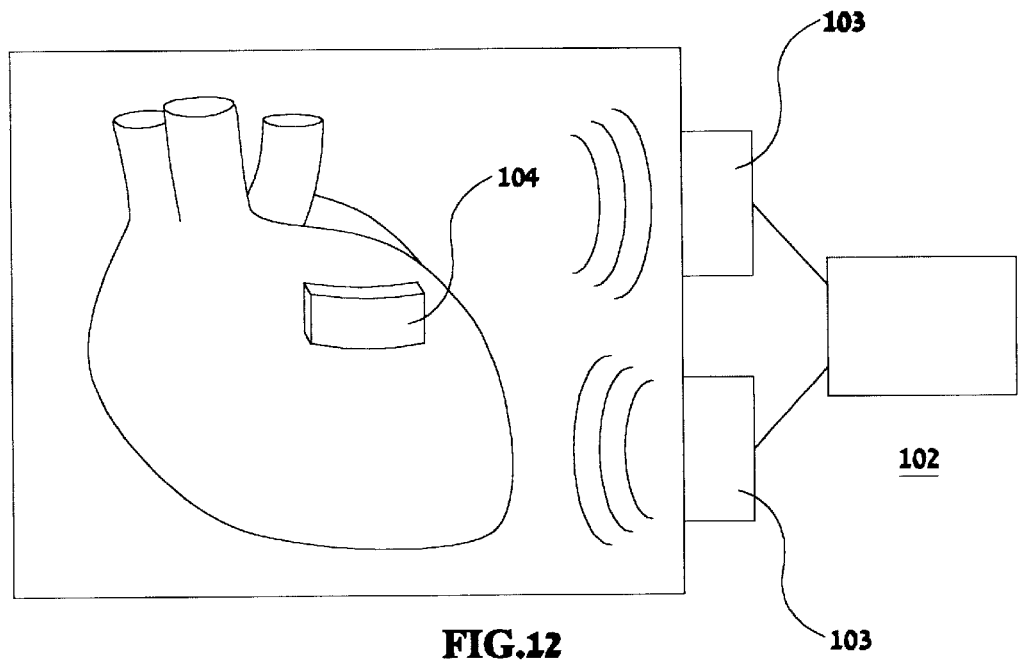
FIG. 12 is a schematic depiction demonstrating the positioning of the telemetry monitoring device on a transplanted organ according to the method of the present invention.
Figure 13A:
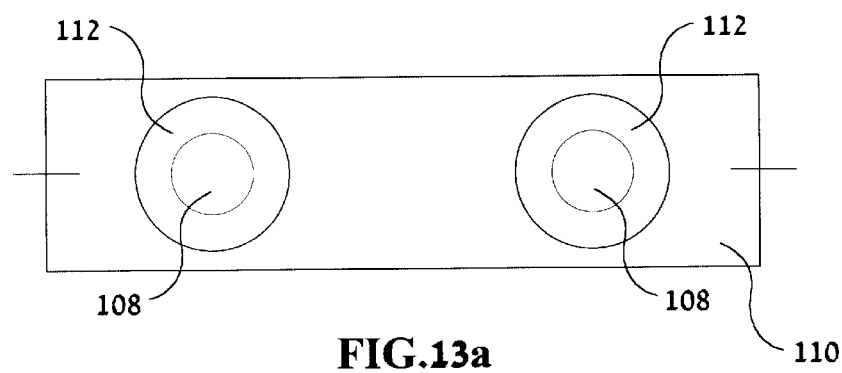
FIG. 13a shows the transplanted organ contact side of the telemetry monitoring unit according to the present invention detailing the electrodes.
Figure 13B:
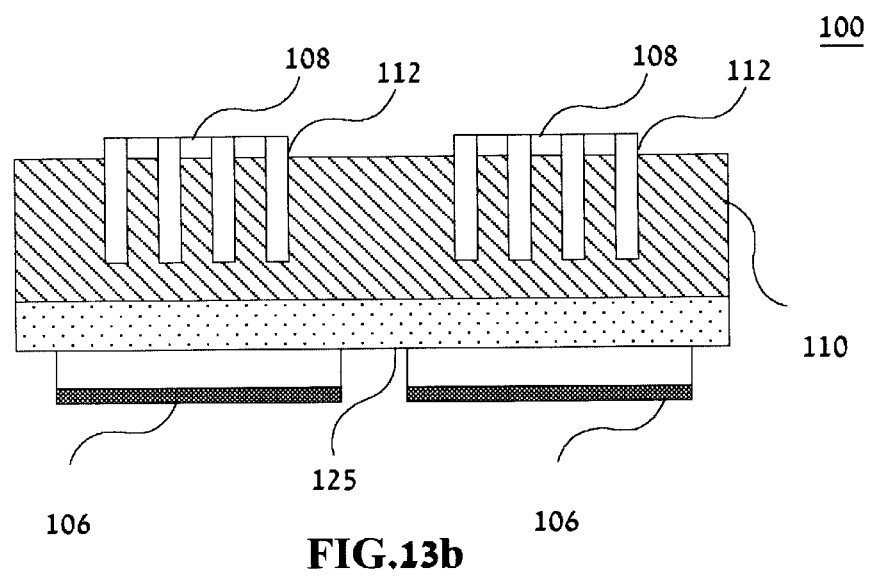

According to preferred embodiments of the present invention and as specifically shown in FIG. 11 telemetry monitoring unit 104 preferably includes, in addition to the above mentioned components, a regulator 120, a detector 122, a control unit 124, a current source 125, a preliminary signal conditioner 126, a multiplexer and modulator 128 and a power amplifier 130.

In more detail, the current obtained from transducer 106 when receiving an acoustic signal is regulate by regulator 120 and then it is provided to electrodes 108 through current source 125 as an alternating current or voltage. Current source 125 serves to regulate the alternating current or voltage provided to electrodes 108. To power telemetry monitoring unit 104 and provide other functions, regulator 120 is incorporated to rectify and regulate the current produced from transducer 106. Standard rectification techniques may be used in conjunction with an appropriate AC-DC converter to preferably obtain voltages in the order of 1–2 Volts. Detector 122 serves for detecting a digitized unique activation code within the received signal, such that when multiple telemetry monitoring units 104 are utilized in one or more patient's only a specific telemetry monitoring unit 104 is activated in response to a specific code. To this end, detector 122 can include a diode or any detector sensitive to modulation methods known in the art such as amplitude modulation.

Following detection, the electrical signal is relayed by detector 122 to control unit 124. Control unit 124 includes logic circuits which perform the following functions: (i) switching unit 104 on and off upon identifying a unique activation code received by detector 122; (ii) switching unit 104 between different possible modes of operation; (iii) carrying out a self-test on command; and (iv) controlling the data channel multiplexing, and any additional control, timing or decision making processes required.

As mentioned above, the converted acoustic signal is relayed as an alternating current or voltage to electrodes 108. This electrical signal is passed through the tissue of the transplanted organ and information pertaining to the impedance amplitude and phase of the tissue is collected.

This information is relayed by electrodes 112 to preliminary signal conditioner 126 which serves for conditioning the signal by improving the signal-to-noise ratio.

Once conditioned, the electrical signals which contain information pertaining to the tissue impedance, such as capacitance, resistance and/or other relevant parameters are relayed using separate data channels to multiplexer and modulator 128. Following collection, the data channels are multiplexed to form a single data channel, which is passed through power amplifier 130, which amplifies the signal to a power level suitable for transmission. The amplified electrical signal is then converted transmitted as an acoustic signal by transducer 106'.

Since the data is transmitted as an acoustic signal through the body of the patient, which is, in effect, a water body, transmission can be effected very efficiently and with considerably little energy expenditure and losses.

It will be appreciated in this respect that acoustic transmission inside an acoustically transparent fluid medium is particularly efficient relative to the amount of energy expended. In order to obtain an acoustic pressure of p Pascal at a distance of r meters from a spherical sound source one requires:

$$P = \frac{4\pi r^2 p^2}{\rho c} \text{ watts}$$

where $\rho$ is the fluid density and c the sound velocity in that fluid. For a pressure of p=1 Pascal, distance of r=25 cm and the acoustic properties of water one obtains P=0.5 $\mu$W of acoustic power. Thus, the transmitter will require only a few $\mu$W of power to generate a clear signal which can be easily picked up outside the body. This permits transplanting the device at any depth within the body and obviates the need for a transplantable power source and/or underskin positionable intrabody component wired to a second intrabody component positionable close to the transplanted tissue as is the case in, for example, U.S. Pat No. 5,246,008.

To multiplex and modulate the data, multiplexer and modulator 128 complexes two or more signals into a single signal transmittable using a single communication channel of telemetry monitoring unit 106'. This is preferably achieved by multiplexing in, for example, frequency or in time. This multiplexing is preferably performed on command from telemetry control unit 102. Such a command, which is preferably provided within the acoustic signal itself, determines which signal or combination of signals will be transmitted by transducer 106' at any given time.

Following multiplexing, and prior to transmission, the data stream is preferably made ready for transmission by modulating the transmitted signal with the data stream. Several methods can be incorporated by the present invention to effect modulation, such as for example, but not limited to, simple amplitude modulation or frequency modulation.

Preferably, frequency-shift keying (FSK) is utilized. By using frequency-shift keying, a frequency redundancy can be generated by using orthogonal symbols, and as such this method is less sensitive to channel instabilities and provides improved signal-to-noise ratio.

In addition, the transmission bandwidth is preferably lowered so as to simplify the transmission process.

It will be appreciated that the field of signal modulation is nowadays very well known in the art, and as such it is presently possible to tailor the modulator to the individual requirements of the data channel.

Figure 14:
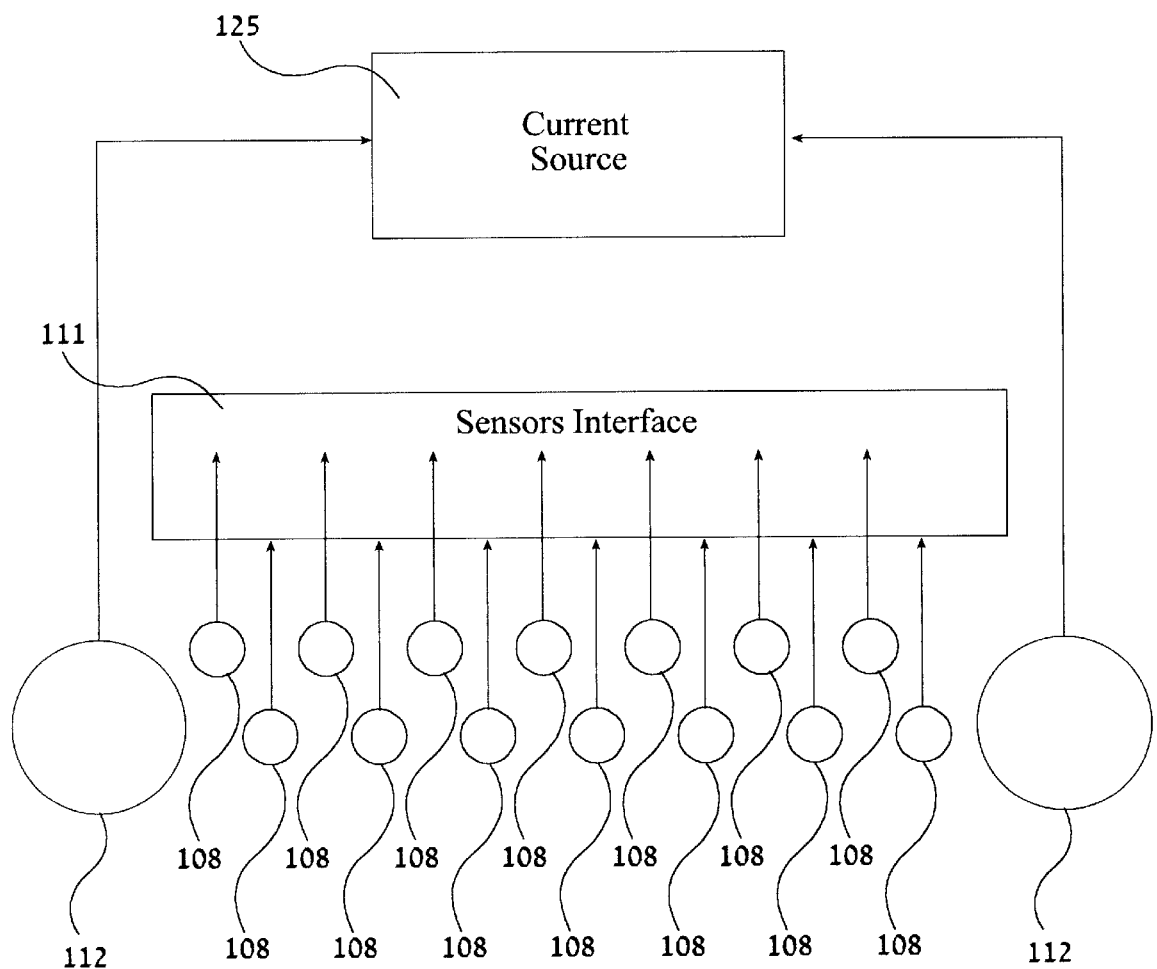
FIG. 14 is a schematic depiction of a grid of electrodes used in a preferred embodiment of the telemetry monitoring unit according to the present invention.

As shown in FIG. 14, according to a preferred embodiment of the present invention electrodes 108 and 112 form a part of an array (grid) of electrodes and are used to measure the tissue impedance at several points, yielding the tissue average impedance and the impedance variance between different points of the transplanted organ. This electrodes arrangement can be fabricated using conventional photolithography methods or micro-machining technology. The array of electrodes includes a current source 125, at least one pair of current electrodes 112 which are used to relay current, preferably alternating current, through the tissue, and a plurality of electrodes 108 that are used to measure the potential drop of the tissue. Electrodes 108 according to this embodiment of the present invention are arranged preferably in rows (at least one row) which form a two dimensional grid. Electrodes 108 are preferably connected to a multi-port sensors interface 111 that transmit the measured value to preliminary signal conditioner 126 and than to control unit 124 and multiplexer and modulator 128.

For telemetry monitoring unit 104 to function properly and efficiently it is preferably miniaturized in size. In addition, it is designed capable of extracting the power necessary for the various functionalities thereof from the impinging extrabody generated acoustic signal. As such, the electronic circuitry can be built around existing ultra-low-power microprocessing cores. For example, unit 104 can be constructed around an XE8851 microcontroller with integrated analog-to-digital converter (Xemics SA of Neuchatel 71-CH-2007, Switzerland). This processor core uses RISC (e.g., CoolRISC™ 816) technology, contains integrated ROM and RAM memory, operates on 1.2 Volts and consumes less than 200 $\mu$A at 1 MHz clock rate, down to less than 30 $\mu$A at 32 kHz clock rate. The surface area of such a processor is just a few mm$^2$.

In addition, the current between the current passing and impedance monitoring electrodes (108 and 112, respectively) can be as low as 1 $\mu$A. Since typical tissue resistance is on the order of a few hundred ohms, a potential drop of a few millivolts will develop between the two impedance monitoring electrodes. Such voltage drop can be for example, amplified by a voltage amplifier which can be integrated into the microprocessor, yielding an energy consumption of less than 1 $\mu$W for impedance monitoring.

Using acoustic transducers also dramatically reduces the energy requirements of telemetry monitoring unit 104.

As further detailed above, a plurality of transducer element 1 units, can be arranged over a surface area of as small as 0.8 mm$^2$ to yield 100–200 $\mu$W of electrical energy. Since the energy requirement of unit 104 is no more than a few $\mu$W of acoustic power, which translates into not more than 10–20 $\mu$W of electrical power, the energy requirement can be easily provided by a plurality of transducer element 1 units incorporated into transducer 106.

Thus, according to the present invention, a possible device configuration can be for example, a cylindrical structure, 2–3 mm in diameter and 3–5 mm in length. Such a structure can readily include the electronic components and at least 20 energy transducer cells, a few of which can double as data transmitters. Such a device is small enough to be implantable in a minimally invasive manner via a standard biopsy needle.

Finally, the values measured by the intra body telemetry unit and which are transmitted to the extracorporeal telemetry control unit can be evaluated directly in the control unit, if the control unit is located in a clinic and operated by specialized personnel.

Preferably, however, the telemetry control unit is connected via data telecommunication to the clinic and the measured values stored in the telemetry control unit can be called in for evaluation by the clinic via data telecommunication. Thus the measurements for monitoring of a rejection reaction that may occur can be performed by the patient at home, preferably during the night time periods of rest. The evaluation of the measurement can be performed later in the clinic at any desired time. Thus monitoring at short time intervals is possible without the need for time-consuming and repetitive visits to the clinic. Data communication via telephony and computer networks is well known in the art of communication and requires no further description herein.

Thus, the telemetry system for monitoring a rejection reaction of a transplanted organ according to the present invention provides an efficient and accurate means for determining the presence or absence of such a reaction. The present invention incorporates the use of acoustic transducers for converting an acoustic power signal which is readily propargatable through the human body, into electrical power for powering and operating the intrabody monitoring device thereof. As such, the intrabody monitoring device of the present invention requires no other power source, such as a battery, or a hardwire connection to a powering unit located outside the body. This in turn enables the device of the present invention to be constructed small enough to be implantable in a minimally invasive manner. In addition, the present invention provides a system which operates efficiently in monitoring a rejection reaction of a transplanted organ at any depth within the body. It will be appreciated that the latter feature of the present invention is of importance because, evolution assured that vital organs are positioned deep within the body, so as to be less rendered to injuries from external sources.

In addition, since the system according to the present invention does not employ an internal energy source that has a finite capacity of energy, it is possible to use the system for frequent, say daily, rejection monitoring. Having such information accessible, it is possible to precisely control the dose of immunosuppressive drugs administered and increase the dose only in response to actual signs of rejection as detected by the system of the present invention. Since immunosuppressive drugs have many deleterious side effects, optimization of their administration is highly advantageous.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A telemetry system for monitoring a rejection reaction of a transplanted organ being transplanted within a patient's body, the telemetry system comprising:
   (a) a telemetry control unit located outside the body of the patient; and
   (b) a telemetry monitoring unit implanted within the body of the patient, said telemetry monitoring unit including:
      (i) at least one acoustic transducer being for receiving an acoustic signal from said telemetry control unit and converting said acoustic signal into a first electrical signal, said at least one acoustic transducer further being for receiving a second electrical signal and converting said second electrical signal into a transmitted acoustic signal receivable by said telemetry monitoring unit; and
      (ii) a plurality of electrodes positionable in intimate contact with, or deep within, the transplanted organ and being in communication with said at least one acoustic transducer, said plurality of electrodes being for passing said first electrical signal through the transplanted organ for monitoring the electrical impedance thereof and further being for relaying said second electrical signal corresponding to said electrical impedance to said at least one acoustic transducer so as to enable the monitoring of the presence or absence of the rejection reaction.

2. The monitoring system of claim 1, wherein the transplanted organ is an internal organ.

3. The monitoring system of claim 2, wherein said internal organ is selected from the group consisting of a heart, a kidney, a liver and a lung.

4. The monitoring system of claim 1, wherein each of said at least one acoustic transducer includes:
   (i) a cell member having a cavity;
   (ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and
   (iii) a first electrode attached to said external surface and a second electrode attached to said internal surface.

5. The monitoring system of claim 1, wherein said first electrical signal is passed through the transplanted organ by a first pair of said plurality of electrodes and further wherein said second electrical signal is relayed by a second pair of said plurality of electrodes.

6. The monitoring system of claim 5, wherein said first pair of said plurality of electrodes and said second pair of said plurality of electrodes are a single pair of electrodes.

7. The monitoring system of claim 1, wherein said first electrical signal is supplied as an alternating electrical current, such that a phase shift of the voltage relative to the current phase indicative of the impedance is relayed by the second electrical signal.

8. The monitoring system of claim 1, wherein said first electrical signal is a substantially square wave pulse electrical current, such that a change in said pulse's amplitude and or phase shift of the complex impedance value indicative of the impedance is relayed by the second electrical signal.

9. The monitoring system of claim 8, wherein the height of the leading edges of said square wave pulse are relayed by said second electrical signal and monitored.

10. The monitoring system of claim 8, wherein the steepness of the leading edges of said square wave pulse are relayed by said second electrical signal and monitored.

11. The system of claim 1, wherein said plurality of electrodes are arranged in a grid form.

12. A method of monitoring a rejection reaction of a transplanted organ being transplanted within a patient's body, the method comprising the steps of:

(a) implanting a telemetry monitoring unit including a plurality of electrodes and at least one acoustic transducer communicating therewith within a patient's body, said plurality of electrodes being in intimate contact with, or deep within, the transplanted organ; and (b) locating a telemetry control unit located outside, and in intimate contact with, the body of the patient;

(c) generating an acoustic signal via said telemetry control unit, said acoustic signal impinging on said at least one transducer of said telemetry monitoring unit, being transduced into a first electrical signal, being relayed to said plurality of electrodes and being passed through the transplanted organ to thereby provide information pertaining to an impedance of the transplanted organ in a form of a second electrical signal being relayed from said plurality of electrodes to said at least one transducer; and (d) receiving via said telemetry control unit a second acoustic signal being transmitted thereto by said at least one transducer, said second acoustic signal corresponding to said second electrical signal.

13. The method of claim 12, wherein the transplanted organ is an internal organ.

14. The method of claim 12, wherein said internal organ is selected from the group consisting of a heart, a kidney, a liver and a lung.

15. The method of claim 12, wherein said at least one acoustic transducer includes:

(i) a cell member having a cavity;

(ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and (iii) a first electrode attached to said external surface and a second electrode attached to said internal surface.

16. The method of claim 12, wherein said first electrical signal is passed by a first pair of said plurality of electrodes and further wherein said second electrical signal is relayed by a second pair of said plurality of electrodes.

17. The method of claim 16, wherein said first pair of said plurality of electrodes and said second pair of said plurality of electrodes are a single pair of electrodes.

18. The method of claim 12, wherein said first electrical signal is supplied as an alternating electrical current, such that a phase shift of the voltage relative to the current phase indicative of the impedance is relayed by the second electrical signal.

19. The method of claim 12, wherein said first electrical signal is a substantially square wave pulse electrical current, such that a change in said pulse's amplitude and or phase shift of the complex impedance value indicative of the impedance is relayed by the second electrical signal.

20. The method of claim 19, wherein the height of the leading edges of said square wave pulse are relayed by said second electrical signal and monitored.

21. The monitoring system of claim 19, wherein the steepness of the leading edges of said square wave pulse are relayed by said second electrical signal and monitored.

* * * * *

UNITED STATES PATENT AND TRADEMARK OFFICE
> ## CERTIFICATE OF CORRECTION

PATENT NO. : 6,198,965 B1
DATED : March 6, 2001
INVENTOR(S) : Penner et al.

It is certified that error appears in the above-identified patent and that said Letters Patent is hereby corrected as shown below:

On the Title Page, in the section entitled Related Application Data insert after 6,140,740: and PCT Application PCT/US98/27669 filed December 28, 1998

Signed and Sealed this

Seventeenth Day of July, 2001

*Attest:*

Nicholas P. Godici

NICHOLAS P. GODICI
*Attesting Officer*    *Acting Director of the United States Patent and Trademark Office*